US012127758B2

(12) United States Patent
Smith et al.

(10) Patent No.: US 12,127,758 B2
(45) Date of Patent: Oct. 29, 2024

(54) SURGICAL TOOL SYSTEMS, AND METHODS OF USE THEREOF

(71) Applicant: Stryker Corporation, Kalamazoo, MI (US)

(72) Inventors: Conrad Smith, Hollister, CA (US); Brian Fouts, Morgan Hill, CA (US); Sunny Jay, Park Gate (IE); Bryan Deeny, Ballincollig (IE)

(73) Assignee: Stryker Corporation, Portage, MI (US)

( * ) Notice: Subject to any disclaimer, the term of this patent is extended or adjusted under 35 U.S.C. 154(b) by 867 days.

(21) Appl. No.: 17/215,275

(22) Filed: Mar. 29, 2021

(65) Prior Publication Data
US 2021/0212713 A1    Jul. 15, 2021

Related U.S. Application Data

(63) Continuation of application No. 16/052,988, filed on Aug. 2, 2018, now Pat. No. 11,000,305.
(Continued)

(51) Int. Cl.
*A61B 17/32* (2006.01)
*A61B 1/04* (2006.01)
(Continued)

(52) U.S. Cl.
CPC ........ *A61B 17/32002* (2013.01); *A61B 1/044* (2022.02); *A61B 17/1659* (2013.01); *A61B 90/39* (2016.02); *A61B 1/04* (2013.01); *A61B 2017/00398* (2013.01); *A61B 2017/00477* (2013.01); *A61B 17/1671* (2013.01); *A61B 2017/320004* (2013.01); *A61B 2017/320028* (2013.01); *A61B 2017/32004* (2013.01); *A61B 17/3207* (2013.01); *A61B 17/320783* (2013.01);
(Continued)

(58) Field of Classification Search
CPC .......... A61B 17/32002; A61B 17/1659; A61B 17/1671; A61B 17/3207; A61B 17/320783; A61B 2017/320004; A61B 2017/320028; A61B 2017/00261; A61B 1/044; A61B 2217/005
USPC .... 606/79–85, 167, 170, 171, 176, 177, 180
See application file for complete search history.

(56) References Cited

U.S. PATENT DOCUMENTS 372,400 A    11/1887  Browne
533,573 A    2/1895   Wilkens
(Continued)

FOREIGN PATENT DOCUMENTS

AU    3781400 A    7/2000
CA    2398850 A1   8/2001
(Continued)

OTHER PUBLICATIONS

"The Formula For Success" Core Arthroscopic System Brochure, Stryker Endoscopy, copyright 2007.
(Continued)

*Primary Examiner* — Marcela I. Shirsat
(74) *Attorney, Agent, or Firm* — Lerner David LLP

(57) ABSTRACT

Surgical tool systems and methods of use thereof for performing endoscopic surgical procedures, which systems include a handpiece and a surgical accessory which detachably connects to the handpiece. The surgical accessory has a distal end which defines a cutting head incorporating two different types of tissue-treating areas.

20 Claims, 16 Drawing Sheets

Related U.S. Application Data

(60) Provisional application No. 62/540,303, filed on Aug. 2, 2017.

(51) Int. Cl.
*A61B 17/00* (2006.01)
*A61B 17/16* (2006.01)
*A61B 17/3207* (2006.01)
*A61B 90/00* (2016.01)

(52) U.S. Cl.
CPC . *A61B 2090/3941* (2016.02); *A61B 2217/005* (2013.01)

(56) References Cited

U.S. PATENT DOCUMENTS

| | | | |
|---|---|---|---|
| 3,384,085 A | 5/1968 | Hall | |
| 3,732,858 A | 5/1973 | Banko | |
| 3,835,858 A | 9/1974 | Hagen | |
| 3,844,272 A | 10/1974 | Banko | |
| 4,030,503 A | 6/1977 | Clark, III | |
| 4,445,509 A | 5/1984 | Auth | |
| 4,646,738 A | 3/1987 | Trott | |
| 4,649,919 A | 3/1987 | Thimsen et al. | |
| 4,842,578 A | 6/1989 | Johnson et al. | |
| 4,844,064 A | 7/1989 | Thimsen et al. | |
| 4,867,157 A | 9/1989 | McGurk-Burleson et al. | |
| 4,983,179 A | 1/1991 | Sjostrom | |
| 5,084,052 A | 1/1992 | Jacobs | |
| 5,112,299 A | 5/1992 | Pascaloff | |
| 5,122,134 A | 6/1992 | Borzone et al. | |
| 5,217,479 A | 6/1993 | Shuler | |
| 5,269,798 A | 12/1993 | Winkler | |
| 5,364,395 A | 11/1994 | West, Jr. | |
| 5,366,468 A | 11/1994 | Fucci et al. | |
| 5,403,317 A | 4/1995 | Bonutti | |
| 5,437,630 A | 8/1995 | Daniel et al. | |
| 5,489,291 A | 2/1996 | Wiley | |
| 5,492,527 A | 2/1996 | Glowa et al. | |
| 5,592,727 A | 1/1997 | Glowa et al. | |
| 5,601,583 A | 2/1997 | Donahue et al. | |
| 5,620,447 A | 4/1997 | Smith et al. | |
| 5,643,303 A | 7/1997 | Donahue | |
| 5,693,063 A | 12/1997 | Van Wyk et al. | |
| 5,759,185 A | 6/1998 | Grinberg | |
| 5,766,199 A | 6/1998 | Heisler et al. | |
| 5,792,167 A | 8/1998 | Kablik et al. | |
| 5,833,692 A | 11/1998 | Cesarini et al. | |
| 5,833,702 A | 11/1998 | Van Wyk et al. | |
| 5,843,106 A | 12/1998 | Heisler | |
| 5,851,208 A | 12/1998 | Trott | |
| 5,913,867 A | 6/1999 | Dion | |
| 5,922,003 A | 7/1999 | Anctil et al. | |
| 5,961,532 A | 10/1999 | Finley et al. | |
| 6,001,116 A | 12/1999 | Heisler et al. | |
| 6,053,923 A | 4/2000 | Veca et al. | |
| 6,053,928 A | 4/2000 | Van Wyk et al. | |
| 6,068,641 A | 5/2000 | Varsseveld | |
| 6,183,487 B1 | 2/2001 | Barry et al. | |
| 6,217,598 B1 | 4/2001 | Berman et al. | |
| 6,312,438 B1 | 11/2001 | Adams | |
| 6,312,441 B1 | 11/2001 | Deng | |
| 6,565,588 B1 | 5/2003 | Clement et al. | |
| 6,569,177 B1 | 5/2003 | Dillard et al. | |
| 6,579,298 B1 | 6/2003 | Bruneau et al. | |
| 6,620,180 B1 | 9/2003 | Bays et al. | |
| 6,638,289 B1 | 10/2003 | Johnson et al. | |
| 6,663,628 B2 | 12/2003 | Peters | |
| 6,827,725 B2 | 12/2004 | Batchelor et al. | |
| 6,979,332 B2 | 12/2005 | Adams | |
| 7,077,845 B2 | 7/2006 | Hacker et al. | |
| 7,237,990 B2 | 7/2007 | Deng | |
| 7,618,428 B2 | 11/2009 | O'Quinn et al. | |
| 7,682,333 B2 | 3/2010 | Deng | |
| 7,803,170 B2 | 9/2010 | Mitusina | |
| 7,887,559 B2 | 2/2011 | Deng et al. | |
| 7,927,361 B2 | 4/2011 | Oliver et al. | |
| 7,993,360 B2 | 8/2011 | Hacker et al. | |
| 8,062,319 B2 | 11/2011 | O'Quinn et al. | |
| 8,177,803 B2 | 5/2012 | Heisler | |
| 8,277,474 B2 | 10/2012 | Norman et al. | |
| 8,414,606 B2 | 4/2013 | Shadeck et al. | |
| 8,435,259 B2 | 5/2013 | Dierck | |
| 9,186,166 B2 | 11/2015 | Thistle | |
| 9,232,952 B2 | 1/2016 | Kulas et al. | |
| 9,636,131 B2 | 5/2017 | Manley et al. | |
| 9,656,008 B2 | 5/2017 | Wulfman et al. | |
| 9,681,913 B2 | 6/2017 | Orczy-Timko et al. | |
| 9,687,254 B2 | 6/2017 | Shadeck et al. | |
| 9,737,322 B2 | 8/2017 | Oliver et al. | |
| 9,839,441 B2 | 12/2017 | Hayes et al. | |
| 10,022,140 B2 | 7/2018 | Germain et al. | |
| 10,052,149 B2 | 8/2018 | Germain et al. | |
| 10,179,002 B2 | 1/2019 | Wasicek et al. | |
| 2002/0029055 A1* | 3/2002 | Bonutti | A61B 10/025 606/170 |
| 2003/0135151 A1 | 7/2003 | Deng | |
| 2004/0092991 A1 | 5/2004 | Deng | |
| 2004/0220602 A1 | 11/2004 | Deng et al. | |
| 2005/0065538 A1 | 3/2005 | Van Wyk | |
| 2005/0222598 A1 | 10/2005 | Ho et al. | |
| 2006/0142775 A1 | 6/2006 | Heneberry et al. | |
| 2006/0196038 A1 | 9/2006 | Van Wyk | |
| 2006/0212060 A1 | 9/2006 | Hacker et al. | |
| 2007/0010822 A1 | 1/2007 | Zalenski et al. | |
| 2008/0208194 A1 | 8/2008 | Bickenbach | |
| 2010/0298855 A1 | 11/2010 | Dierck | |
| 2011/0238099 A1 | 9/2011 | Loreth | |
| 2012/0101513 A1* | 4/2012 | Shadeck | A61B 17/1659 606/180 |
| 2012/0150209 A1 | 6/2012 | Gubellini et al. | |
| 2012/0203230 A1 | 8/2012 | Adams | |
| 2013/0274779 A1 | 10/2013 | Kulas et al. | |
| 2014/0277041 A1* | 9/2014 | Manley | A61B 17/32002 606/170 |
| 2015/0327881 A1 | 11/2015 | Willhite et al. | |
| 2016/0106453 A1 | 4/2016 | Deeny et al. | |
| 2017/0056026 A1 | 3/2017 | Vu et al. | |
| 2017/0202612 A1 | 7/2017 | Germain et al. | |
| 2017/0252099 A1 | 9/2017 | Orczy-Timko et al. | |

FOREIGN PATENT DOCUMENTS

| | | |
|---|---|---|
| CA | 2361354 A1 | 5/2002 |
| DE | 69732580 T2 | 5/2006 |
| EP | 276478 A1 | 8/1988 |
| EP | 0796064 A1 | 9/1997 |
| EP | 0800793 A1 | 10/1997 |
| EP | 0836833 A2 | 4/1998 |
| EP | 1006898 B1 | 6/2000 |
| EP | 1253863 B1 | 11/2002 |
| EP | 1676537 A1 | 7/2006 |
| EP | 1702573 A1 | 9/2006 |
| EP | 2470085 A1 | 7/2012 |
| EP | 2484297 A1 | 8/2012 |
| GB | 2093353 A | 9/1982 |
| WO | 9215255 A1 | 9/1992 |
| WO | 9827876 A1 | 7/1998 |
| WO | 0078236 A1 | 12/2000 |
| WO | 0105313 A1 | 1/2001 |
| WO | 2006011119 A1 | 2/2006 |
| WO | 2006102124 A2 | 9/2006 |
| WO | 2009054968 A1 | 4/2009 |
| WO | 2010126882 A1 | 11/2010 |
| WO | 2012054302 A1 | 4/2012 |
| WO | 2013158469 A1 | 10/2013 |

OTHER PUBLICATIONS

International Search Report issued in Application No. PCT/US2018/044952 date of mailing Oct. 12, 2018 (7 pages).

(56) References Cited

OTHER PUBLICATIONS

Written Opinion of International Searching Authority issued in Application No. PCT/US2018/044952 date of mailing Oct. 12, 2018 (10 pages).
Extended European Search Report issued in Appln. No. 22213576.6 mailed Mar. 30, 23 (9 pages).

\* cited by examiner

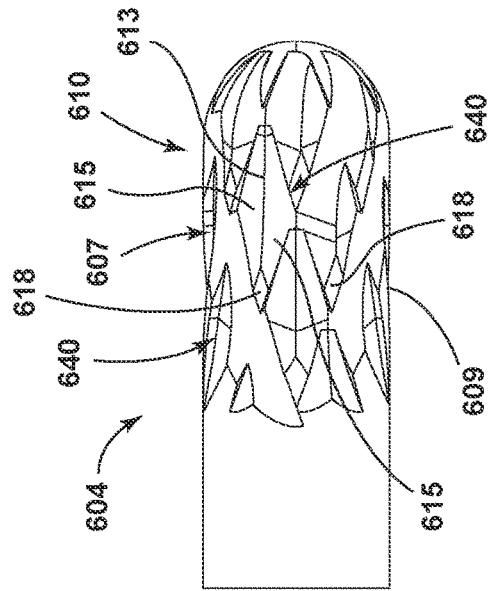

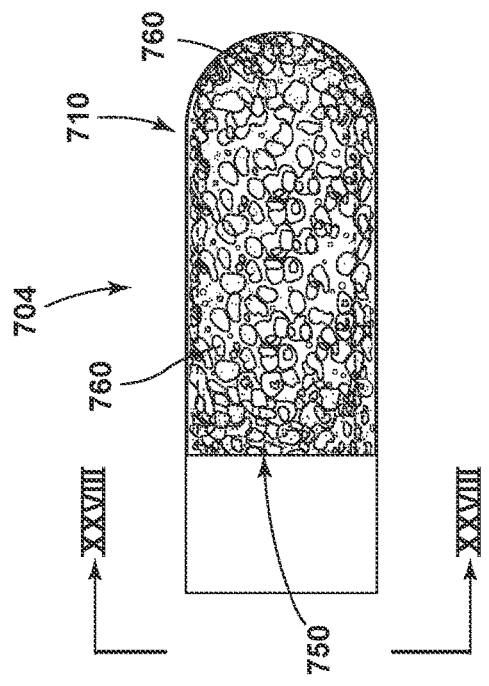
FIG. 25
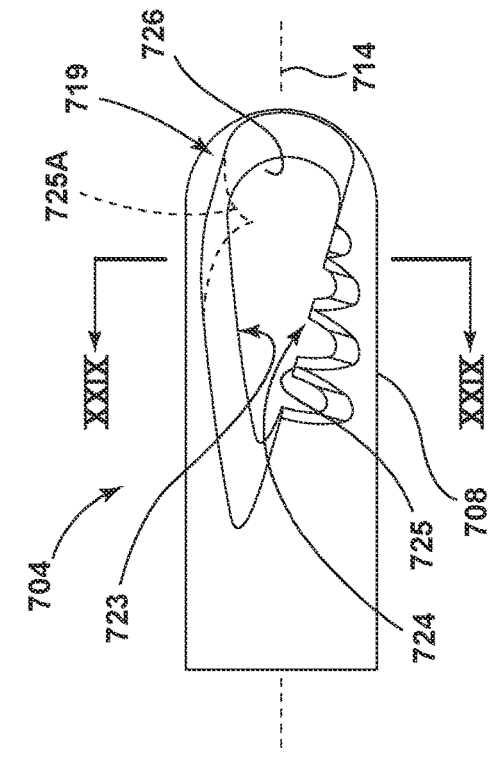
FIG. 26
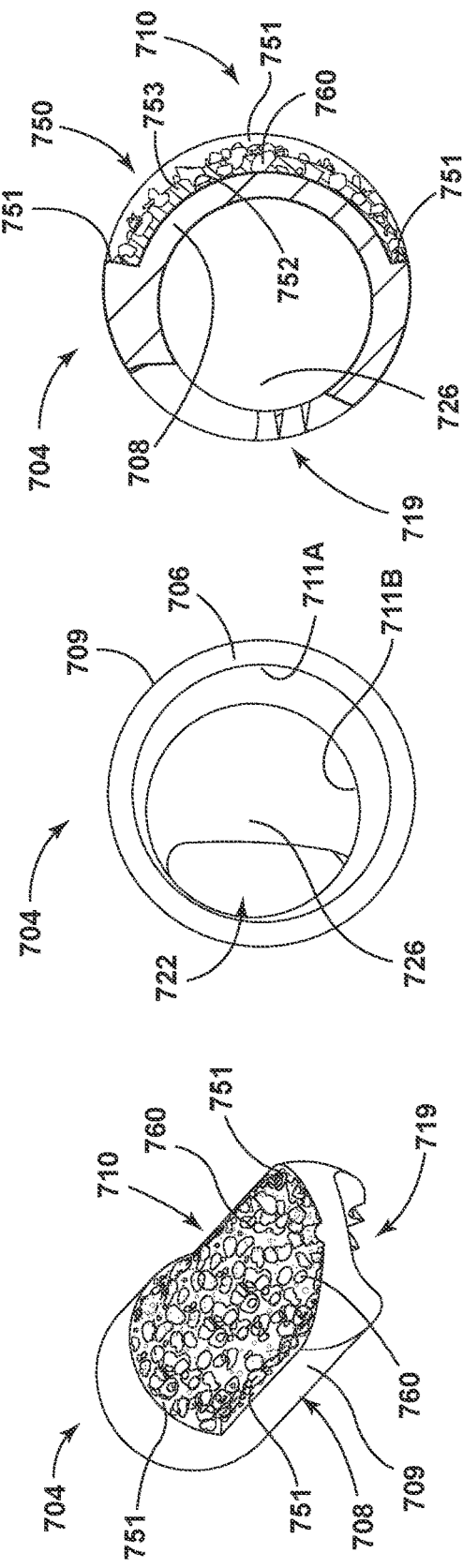
FIG. 28
FIG. 29
FIG. 27

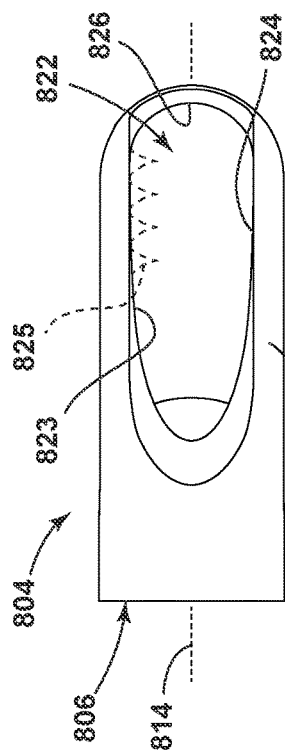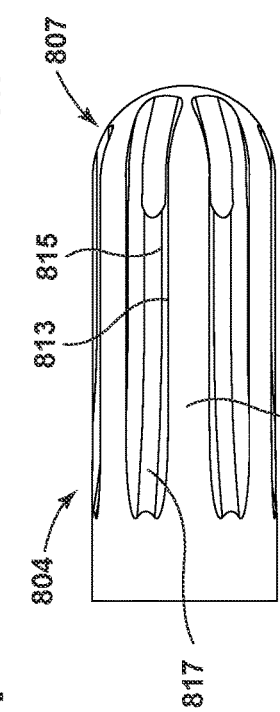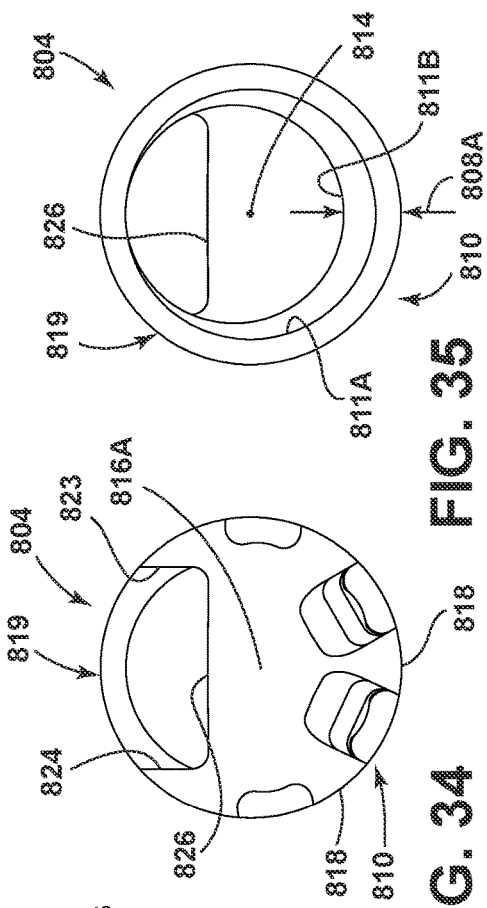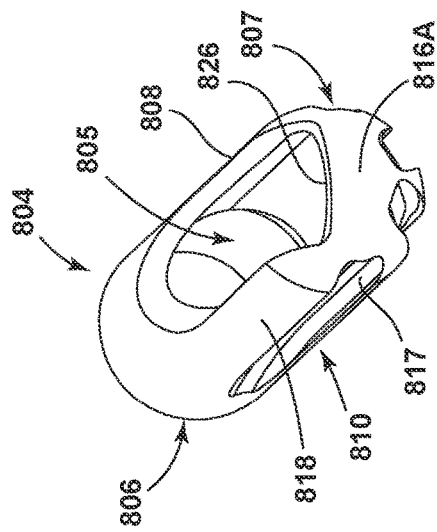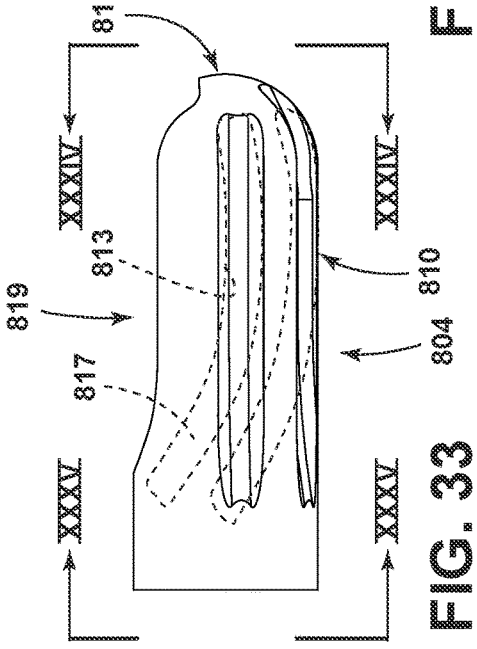

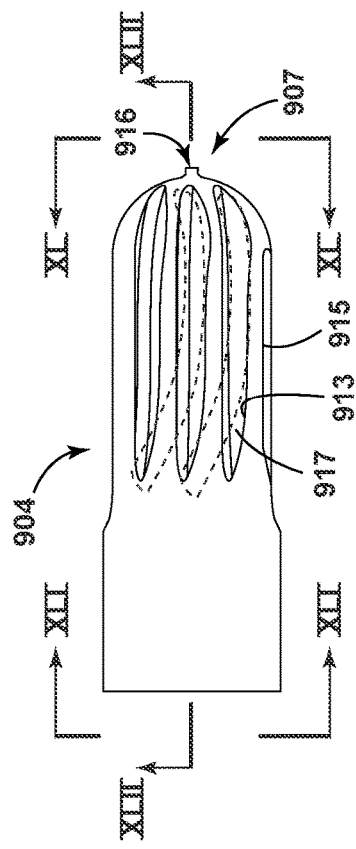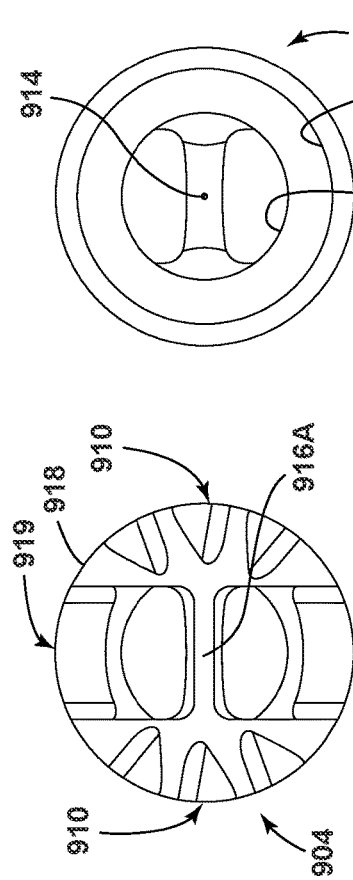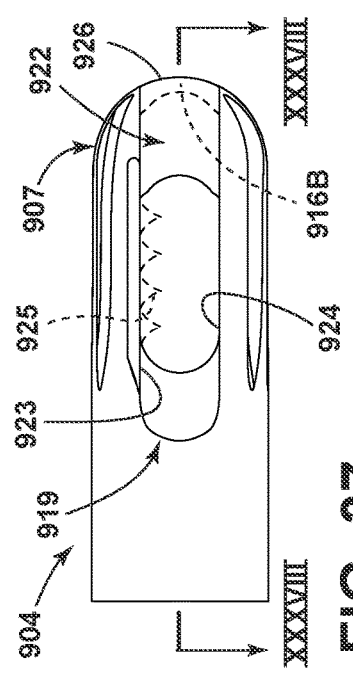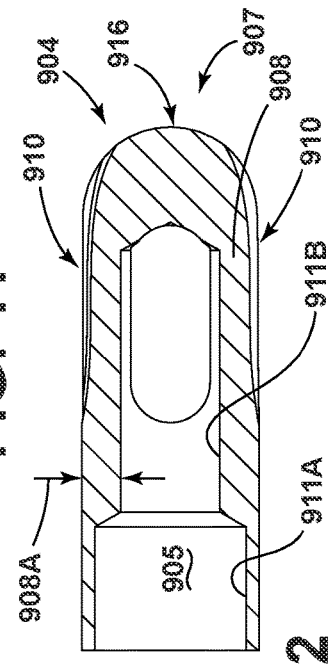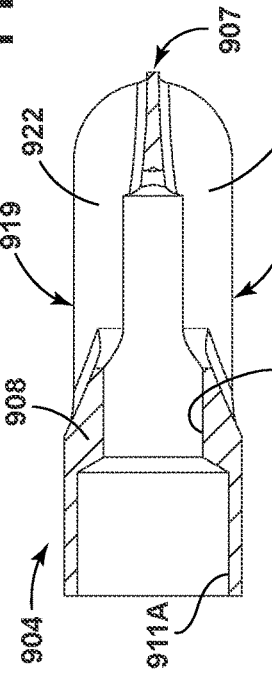

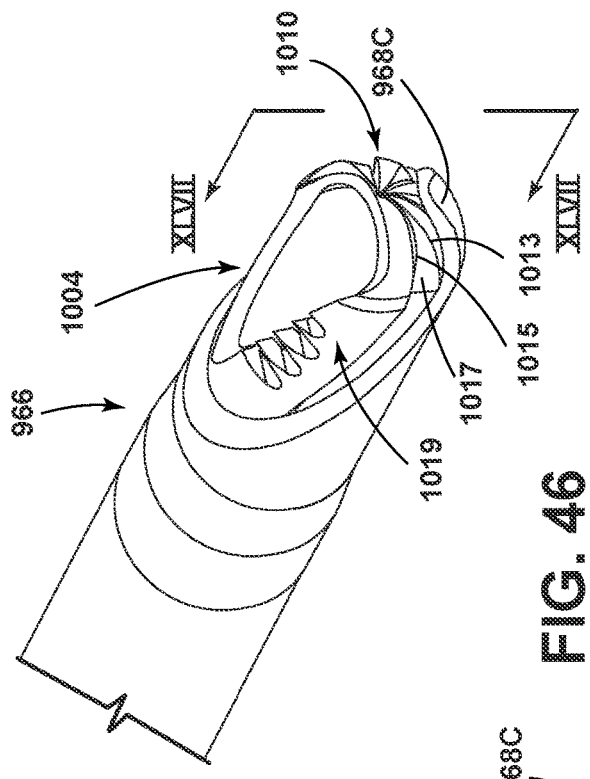
FIG. 46
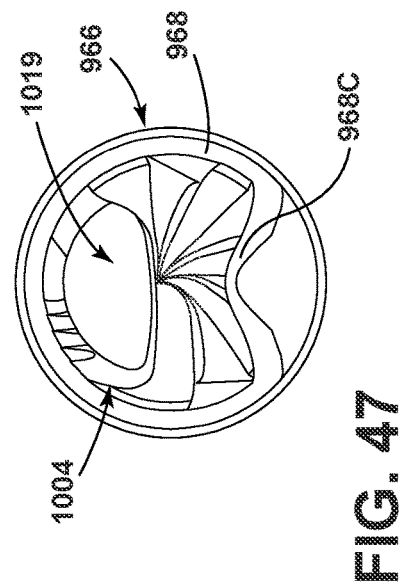
FIG. 47
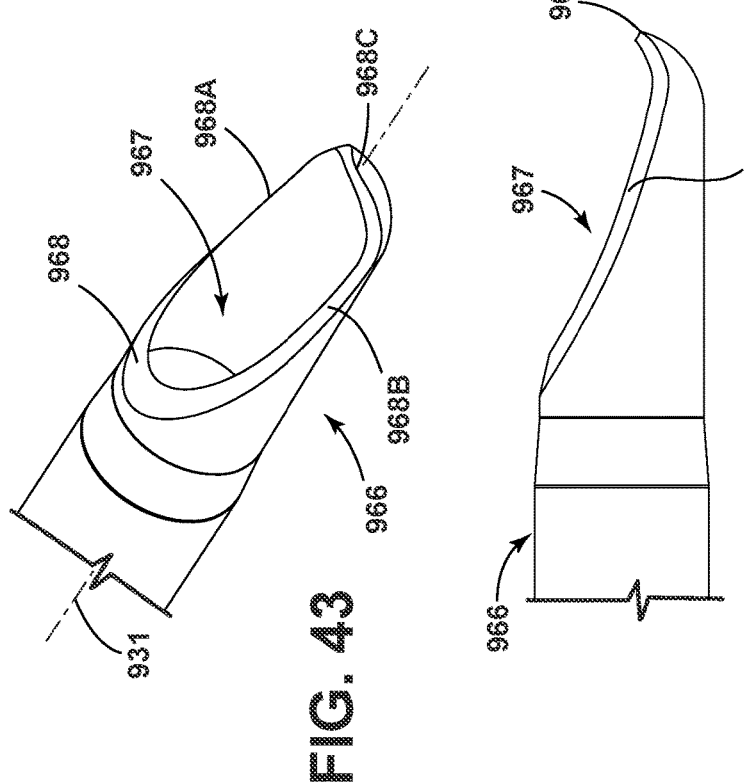
FIG. 43
FIG. 44
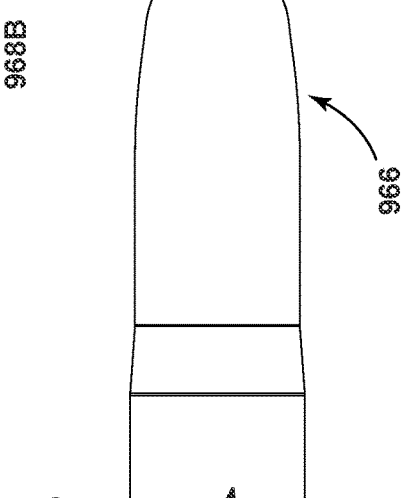
FIG. 45

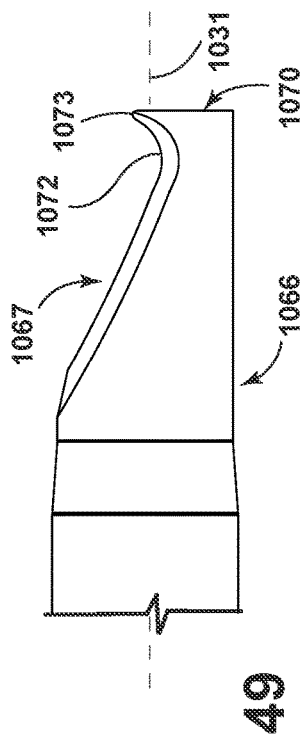
FIG. 49
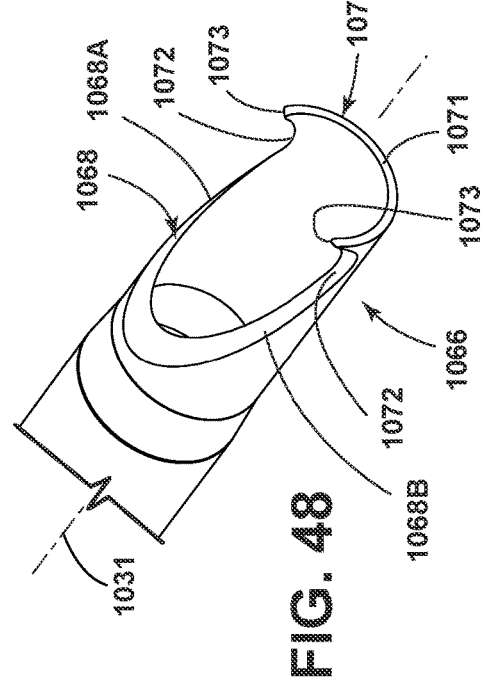
FIG. 48
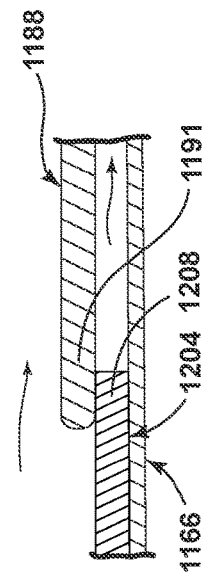
FIG. 50
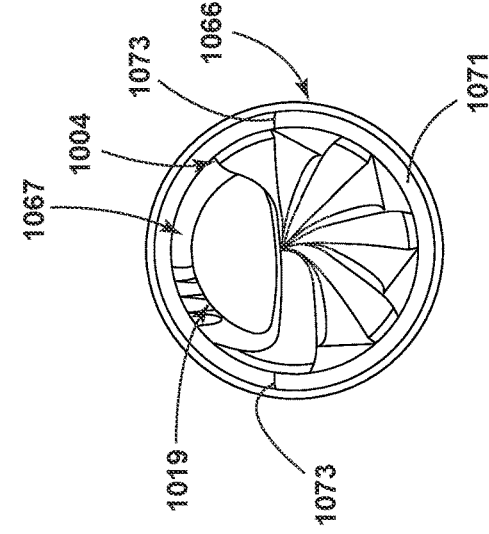
FIG. 51
FIG. 52

SURGICAL TOOL SYSTEMS, AND METHODS OF USE THEREOF

CROSS-REFERENCE TO RELATED APPLICATIONS

This application is a continuation of U.S. patent application Ser. No. 16/052,988, filed Aug. 2, 2018, which claims priority to U.S. Provisional Application Ser. No. 62/540,303, filed on Aug. 2, 2017, the disclosures of which are hereby incorporated by reference herein in their entirety.

TECHNICAL FIELD

This disclosure generally relates to surgical tool systems and methods for performing endoscopic surgical procedures and, more particularly, to tool systems and methods utilizing a surgical accessory which incorporates a cutting head configuration optimized for removing both soft and hard tissue.

BACKGROUND

Endoscopic surgical procedures are routinely performed in order to accomplish various surgical tasks. In such a surgical procedure, small incisions or portals are made in the patient. An endoscope, which is a device that allows medical personnel to view the surgical site, is inserted in one of the portals and surgical instruments used to perform other tasks are inserted into other portals. The surgeon views the surgical site through the endoscope to determine how to manipulate the surgical instruments in order to accomplish the desired procedure. An advantage of performing endoscopic surgery is that, since the portions of the body that are cut open are minimized, the portions of the body that need to heal after the surgery are likewise reduced. Moreover, during an endoscopic surgical procedure, only relatively small portions of the internal organs and tissue are exposed to the open environment. This minimal opening of the body lessens the extent to which the organs and tissue are open to infection.

The ability to perform endoscopic surgery is enhanced by the development of powered surgical tool systems especially designed to perform such procedures. One such exemplary tool system is sold by the assignee hereof under the trademark FORMULA®. This tool system includes a handpiece designed to be held in the hand of the surgeon. The handpiece has a front or distal end provided with a coupling assembly for releasably holding a surgical accessory, and a motor disposed within a handpiece housing which drives the accessory. The surgical accessories, such as shavers, drills and burs, include a hub which defines the proximal end of the accessory and is appropriately configured to cooperate with the coupling assembly of the handpiece to lock the accessory thereto. Such accessories also include an elongated and tubular outer housing element having a proximal end fixed to the hub, and an elongated cutting element including a drive shaft disposed within the housing element. When the accessory is attached to the handpiece, the handpiece motor couples to the drive shaft of the accessory and moves same relative to the outer housing element. The handpiece motor is selectively actuable to drive the accessory drive shaft so as to cause a desired cutting action at the distal end of the accessory. The handpiece is associated with a control unit which controls the functioning thereof, and is actuated by the user via appropriate buttons provided on the handpiece itself, at the control unit or through use of a footswitch.

Mechanical surgical accessories, such as the shaver, drill and bur discussed above, are commonly used in arthroscopic procedures, and allow for the resection of hard and soft bodily tissues, for example, those found within the knee, shoulder and other joints. This type of surgical accessory may be utilized for both soft and hard tissue removal. In a shaver-type surgical accessory, the outer housing element incorporates a window or opening at the distal end, which window is defined by an edge of the wall of the outer housing element. The cutting element drive shaft at the distal end thereof includes a cutting head having a window defined by an edge of the wall of the cutting head. These window edges of the housing and cutting elements are configured to cut tissue, and when the cutting element is disposed within the housing element, the cutting head window is positioned adjacent the window of the housing element. As the drive shaft is moved relative to the housing element by the handpiece motor, the cutting edge of the cutting head window and the opposed and facing cutting edge of the housing element window cause a cutting or scissoring action which effectively severs tissue located within the housing element window and between the opposed cutting edges of the housing element and the cutting head. The configurations of these opposed edges allow for removal of particular tissue types, and a variety of different cutting window geometries are available to specifically address the type of cutting the accessory is to carry out or in accordance with the particular preference of the surgeon. In this regard, the windows of both of the housing element and the cutting head may be provided with straight cutting edges which may be useful for making fine or detailed cuts, and may also be used for removing areas of hard tissue, such as bone. This straight-edge configuration of a shaver-type surgical accessory can also be used to cut soft, fibrous tissue. Alternatively, the windows of both the housing element and the cutting head may be provided with toothed or serrated cutting edges which may achieve a more aggressive cut for removal of soft fibrous tissue. Other arrangements include providing the window of the housing element with a straight cutting edge and the window of the cutting head with a toothed cutting edge. The predominant function of teeth provided on a surgical accessory, and specifically the teeth provided on the cutting head of the inner cutting element of a shaver-type surgical accessory, is to pull tissue towards the cutting edge of the outer housing element window, at which point the tissue is cut by the scissoring action mentioned above.

A bur-type surgical accessory is commonly used to resect bone or other hard tissues, and includes cutting features which, when the accessory is rotated, serve to cut away such tissue. Such cutting features of this type of accessory may be helically or non-helically oriented. Non-helically oriented cutting features may be those which extend linearly or parallel with the axis of the accessory. The cutting element of a bur-type surgical accessory includes a cutting head with these cutting features which, in some accessories, are exposed through a window formed at the distal end of the outer housing element when the cutting element is located therein. In some bur-type surgical accessories, the window formed in the outer housing element opens primarily sidewardly, so that the distal end of the outer housing element covers a portion or one side of the cutting head of the bur to allow the user to better target bone or hard tissue. Alternatively, the entire cutting head geometry may project distally beyond the terminal end of the outer housing element. A variety of bur geometries are available to specifically address the type of cutting the accessory is to carry out.

Additionally, in an endoscopic surgical procedure, irrigating fluid is introduced into the surgical site, which fluid serves as a transport media for removing tissue and debris therefrom. In order to remove the irrigating fluid and the material contained therein, the above-discussed handpiece and the various accessories which are usable therewith together define a suction conduit. In this regard, a suction pump is connected to the handpiece to provide the suction force needed for drawing the fluid and material away from the surgical site. In order to control the suction flow through the accessory and the handpiece, the handpiece is typically provided with a manually operated valve which is manipulated by the surgeon to control suction of material away from the surgical site. In a shaver-type surgical accessory, surgical debris is suctioned away through the aligned windows of the outer housing element and the cutting head of the cutting element, and then evacuated via a passage provided in the surgical accessory. Likewise, some bur-type surgical accessories incorporate a suction arrangement including a suction opening formed in a distal end of the drive shaft and proximally of the cutting head, which suction opening communicates with a hollow interior of the drive shaft. Surgical debris is thus suctioned inwardly into the surgical accessory through this suction opening and then into a passage of the drive shaft and away from the accessory. In other bur-type surgical accessories, such as the one disclosed in U.S. Pat. No. 9,636,131 (owned by the assignee hereof), a suction opening or openings are provided in the cutting head itself adjacent the cutting features thereof.

SUMMARY

While the arrangements described above perform well, there is a continuing desire and need for improved performance in surgical accessories in an effort to minimize trauma to the patient and to make the operative procedure more efficient and effective for both the patient and the surgeon carrying out the procedure. The surgical accessory disclosed herein according to various embodiments is a multi-functional surgical accessory which incorporates two different tissue-treating areas or tissue-treating configurations which together provide the hard tissue removal, resecting, or cutting action and benefits of a bur-type cutting accessory, as well as efficient soft-tissue removal, resection, or cutting and benefits of a shaver-type cutting accessory. Providing this type of geometry on a surgical accessory allows the surgeon to efficiently remove both hard and soft tissue with a single surgical cutting accessory. As such, the number of surgical accessories that are needed during a surgical procedure to achieve the desired result is reduced, which saves time during a procedure, promotes safety during the procedure and reduces overall equipment costs.

There is provided a surgical accessory for treating a first tissue type having a first hardness and for treating a second tissue type having a second hardness less than the first hardness. The surgical accessory includes a cutting element having a proximal end, a distal end spaced therefrom and a cutting head disposed at the distal end and defining a longitudinal axis. The cutting head may include first and second tissue-treating areas spaced from one another along an outer peripheral area thereof which extends about the axis, wherein the first tissue-treating area and the second tissue-treating area are configured differently from one another to provide the cutting head with different types of tissue-treating action. The first tissue-treating area has a region configured for abrading the first tissue type, which abrading region extends along a substantial part of the total of the outer peripheral area of the cutting head, and the second tissue-treating area includes a region configured for treating the second tissue type.

The cutting head of the surgical accessory may include a wall defining a hollow interior portion within the cutting head with the outer peripheral area being formed on the wall, wherein the region of the second tissue-treating area includes a window extending through the wall for communication with the hollow interior portion.

The wall of the cutting head of the surgical accessory may include a pair of edges configured to cut tissue and disposed in opposed and spaced relation with one another at the outer peripheral area, wherein the edges respectively define substantially opposite sides of the window.

The wall of the cutting head of the surgical accessory may be tubular in shape and may extend circumferentially about the axis and terminate at the respective cutting edges of the second tissue-treating area such that the edges thereof define free terminal edges of the wall with the window being disposed therebetween.

The wall of the cutting head of the surgical accessory, at an area corresponding to the first tissue-treating area, may have a greater thickness than a thickness of the wall at the second tissue-treating area.

The first tissue-treating area of the surgical accessory may extend along a substantial circumferential portion of the outer peripheral area of the cutting head and may include a solid and non-windowed portion of the wall which is not in fluid communication with the hollow interior.

The cutting edges of the second tissue-treating area of the surgical accessory may be substantially parallel with one another or may be non-parallel with one another. Further, one or both of the cutting edges of the second tissue-treating area may include at least one tooth.

The surgical accessory may include an outer housing element having a proximal end and a distal end spaced therefrom, the distal end defining a window including a pair of edges configured to cut tissue and disposed in opposed and spaced relation with one another. Further, the cutting head may be disposed within the distal end of the outer housing element such that the cutting edges of the window of the cutting head are disposed to cooperate with the cutting edges of the window of the outer housing element to treat tissue located adjacent the windows during movement of the cutting head relative to the outer housing element.

The abrading region of the first tissue-treating area of the surgical accessory may include a fluted region including a cutting surface and a flute each extending longitudinally along the outer peripheral area of the cutting head. The cutting surface and the flute may each extend along the outer peripheral area either helically about the axis, or linearly so as to be substantially parallel with the axis.

The abrading region of the first tissue-treating area of the surgical accessory may include a plurality of abrasive particles fixed to an exterior surface of the cutting head located on the outer peripheral area thereof.

The abrading region of the first tissue-treating area of the surgical accessory may include a rasp including a plurality of teeth.

The second tissue-treating area of the surgical accessory may be non-fluted.

There is additionally provided a surgical accessory which may include a cutting element having a proximal end, a distal end spaced therefrom and a cutting head disposed at the distal end and defining a longitudinal axis. The cutting head may include a wall defining a hollow interior portion within the cutting head. The cutting head may include first and second tissue-treating areas spaced from one another along an outer peripheral area of the wall of the cutting head, wherein the first tissue-treating area and the second tissue-treating area may be configured differently from one another to provide the cutting head with both hard and soft tissue-treating action. Further, the second tissue-treating area may be non-fluted. The first tissue-treating area may include one of a fluted region or an abrading region, and the second tissue-treating area may include a window extending through the wall for communication with the hollow interior portion. The wall may include a pair of edges configured to cut tissue and disposed in opposed and spaced relation from one another at the outer peripheral area, wherein the edges respectively define substantially opposite sides of the window and form part of the second tissue-treating area.

There is also provided a surgical tool system including a surgical accessory having an outer housing assembly including a hub at a proximal end thereof and an elongate and substantially tubular housing element having a proximal end fixed to the hub and a distal end spaced therefrom, the distal end defining a housing element window, the housing element window being defined partially by a pair of edges of the housing element configured to cut tissue and disposed in spaced relation from one another along a periphery of the distal end. The surgical accessory may further include a cutting element assembly for removing a first tissue type having a first hardness and for removing a second tissue type having a second hardness less than the first hardness. The cutting element assembly may include a hub at a proximal end thereof and a drive shaft disposed within the housing element for movement relative thereto, the drive shaft having a proximal end fixed to the hub of the cutting element assembly and a distal end spaced from the proximal end of the drive shaft. The cutting element assembly may further include a cutting head defining an axis, the cutting head having a hollow interior portion and an exterior portion and having first and second tissue-treating areas spaced peripherally from one another along the exterior portion of the cutting head. The first tissue-treating area includes an abrading region configured for treating the first tissue type, and the second tissue-treating area includes a cutting head window for treating the second tissue type. The cutting head window communicates with the hollow interior portion of the cutting head, and the cutting head window is defined partially by a pair of edges of the cutting head which are configured to cut tissue and are spaced peripherally from one another therealong. The cutting head is disposed within the distal end of the housing element axially adjacent the housing element window such that the cutting edges of the cutting head window are disposed to cooperate with the cutting edges of the housing element window to treat tissue located within the windows during movement of the cutting head relative to the housing element window.

The cutting edges of said cutting head window of the surgical accessory of the surgical tool system may be disposed radially closely adjacent to the cutting edges of the housing element window.

The cutting head of the surgical accessory of the surgical tool system may be rotatably movable relative to and within the distal end of the housing element.

The abrading region of the first tissue-treating area of the surgical accessory of the surgical tool system may include a flute disposed in circumferentially adjacent relation with a cutting surface, and the flute and the cutting surface may extend longitudinally along the cutting head either helically about the axis, or linearly in substantially parallel relation with the axis.

The cutting head of the surgical accessory of the surgical tool system may include a wall which defines the hollow interior portion and through which the cutting element window extends, wherein the wall at an area corresponding to the first tissue-treating area has a greater thickness than a thickness of the wall at respective regions of the wall disposed closely adjacent the edges of the second tissue-treating area.

The abrading region of the cutting head of the surgical accessory of the surgical tool system may include a plurality of alternating cutting surfaces and flutes, with each cutting surface having a terminal outer edge. The wall of the cutting head may define a land immediately adjacent each terminal outer edge, with each land having an outer diameter substantially similar to an inner diameter of an inner surface disposed on the distal end of the housing element. Further, each land may form a bearing surface on the cutting head for cooperation with the inner surface of the housing element during movement of the cutting head relative thereto.

In the surgical tool system, one of the distal end of the housing element of the surgical accessory or the cutting head of the surgical accessory may include a material having a greater hardness than a hardness of a material of the other of the distal end of the housing element or the cutting head.

In the surgical tool system, the abrading region of the first tissue-treating area of the cutting head of the surgical accessory may include a plurality of abrasive particles fixed to the exterior portion of the cutting head.

In the surgical tool system, the abrading region of the first tissue-treating area of the cutting head of the surgical accessory may include a rasp including a plurality of teeth.

In the surgical tool system, the abrading region of the first tissue-treating area of the cutting head of the surgical accessory may extend circumferentially along a substantial portion of the exterior portion of the cutting head and may be a solid and non-windowed portion thereof which is not in communication with the hollow interior portion.

In the surgical tool system, the second tissue-treating area of the cutting head of the surgical accessory may be non-fluted.

The surgical tool system may include a handpiece and a coupling arrangement for interconnecting the handpiece with the surgical accessory.

There is also provided a method of treating tissue at a surgical site, the tissue at the surgical site being of a first tissue type having a first hardness and a second tissue type having a second hardness less than the first hardness. The method includes treating the first tissue type with an abrading region of a first tissue-treating area provided on a cutting head of a single surgical resection tool, the abrading region extending along a substantial part of a total outer peripheral area of the cutting head, and treating the second tissue type with a second tissue-treating area provided on the cutting head of the single surgical resection tool.

The first tissue type includes bone or cartilage or a combination thereof, and the second tissue type includes ligaments, tendons or muscle or a combination thereof. In accordance with the method, the treating of the first tissue type may be performed subsequent to the treating of the second tissue type.

The method may include operating the single surgical accessory in first and second opposite rotational directions when treating the second tissue type.

Additionally, the method may include operating the single surgical accessory in a single rotational direction when treating the first tissue type.

Further, the method may include operating the single surgical accessory in first and second opposite rotational directions to treat the second tissue type, and thereafter operating the single surgical accessory in the first rotational direction to treat the first tissue type.

There is additionally provided a kit for imaging tissue in a surgical site, the kit including the surgical accessory or the surgical tool system.

Also provided is a fluorescence imaging agent, for use with the surgical accessory or the surgical tool system, for imaging tissue in a surgical site.

Still further, the surgical accessory, the surgical tool system or the method of treating tissue may be used in combination with medical imaging, robotics, or a combination thereof, the medical imaging including blood flow imaging, tissue perfusion imaging, tissue anatomy imaging or a combination thereof.

BRIEF DESCRIPTION OF THE DRAWINGS

FIG. 21 is an enlarged and isolated view of a further embodiment of the cutting head of the surgical accessory;

FIG. 22 is an enlarged and isolated view of the cutting head of the surgical accessory rotated approximately 180 degrees from the position shown in FIG. 21;

FIG. 23 is an enlarged and isolated perspective view of the cutting head of the surgical accessory shown in FIGS. 21 and 22;

FIG. 24 is an enlarged cross-sectional view as seen generally along line XXIV-XXIV in FIG. 21;

FIG. 25 is an enlarged and isolated view of a further embodiment of the cutting head of the surgical accessory;

FIG. 26 is an enlarged and isolated view of the cutting head of the surgical accessory rotated approximately 180 degrees from the position shown in FIG. 25;

FIG. 27 is an enlarged and isolated perspective view of the cutting head of the surgical accessory shown in FIGS. 25 and 26;

FIG. 28 is an enlarged proximal end view as seen generally along line XXVIII-XXVIII in FIG. 26;

FIG. 29 is an enlarged cross-sectional view as seen generally along line XXIX-XXIX in FIG. 25;

FIG. 30 is an enlarged perspective view of a further embodiment of the cutting head of the surgical accessory;

FIG. 31 is an enlarged plan view of the cutting head of the surgical accessory of FIG. 30;

FIG. 32 is an enlarged view of the cutting head of the surgical accessory rotated approximately 180 degrees from the position shown in FIG. 31;

FIG. 33 is an enlarged view of the cutting head of the surgical accessory rotated approximately 90 degrees from the position shown in FIG. 31;

FIG. 34 is an enlarged distal end view as seen along line XXXIV-XXXIV in FIG. 33;

FIG. 35 is an enlarged proximal end view as seen along line XXXV-XXXV in FIG. 33;

FIG. 36 is an enlarged perspective view of a further embodiment of the cutting head of the surgical accessory;

FIG. 37 is an enlarged plan view of the cutting head of the surgical accessory of FIG. 36;

FIG. 38 is a cross-sectional view as seen generally along line XXXVIII-XXXVIII in FIG. 37;

FIG. 39 is an enlarged view of the cutting head of the surgical accessory rotated approximately 180 degrees from the position shown in FIG. 37;

FIG. 40 is an enlarged distal end view as seen along line XL-XL in FIG. 39;

FIG. 41 is an enlarged proximal end view as seen along line XLI-XLI in FIG. 39;

FIG. 42 is a cross-sectional view as seen generally along line XLII-XLII in FIG. 39;

FIG. 43 is an enlarged perspective view of a further embodiment of the surgical accessory, including a variation of the distal end of the outer housing element shown in isolation;

FIG. 44 is an enlarged side view of the surgical accessory of FIG. 43;

FIG. 45 is an enlarged view of the surgical accessory, rotated approximately 90 degrees from the position shown in FIG. 44;

FIG. 46 is an enlarged and fragmentary perspective view of the surgical accessory of FIGS. 43-45, including a further variation of a cutting head located within the outer housing element;

FIG. 47 is an enlarged distal end view as seen along line XLVII-XLVII in FIG. 46;

FIG. 48 is an enlarged and isolated perspective view of a further embodiment of the surgical accessory, including a further variation of the distal end of the outer housing element shown in isolation;

FIG. 49 is an enlarged side view of the surgical accessory of FIG. 48;

FIG. 50 is an enlarged and fragmentary perspective view of the surgical accessory of FIGS. 48 and 49, including the cutting head of the embodiment of FIGS. 46 and 47 located within the outer housing element;

FIG. 51 is an enlarged distal end view as seen along line LI-LI in FIG. 50;

FIG. 52 is an enlarged and fragmentary cross-sectional view of a variation of the drive shaft shown in FIGS. 2 and 4;

Figure 1:
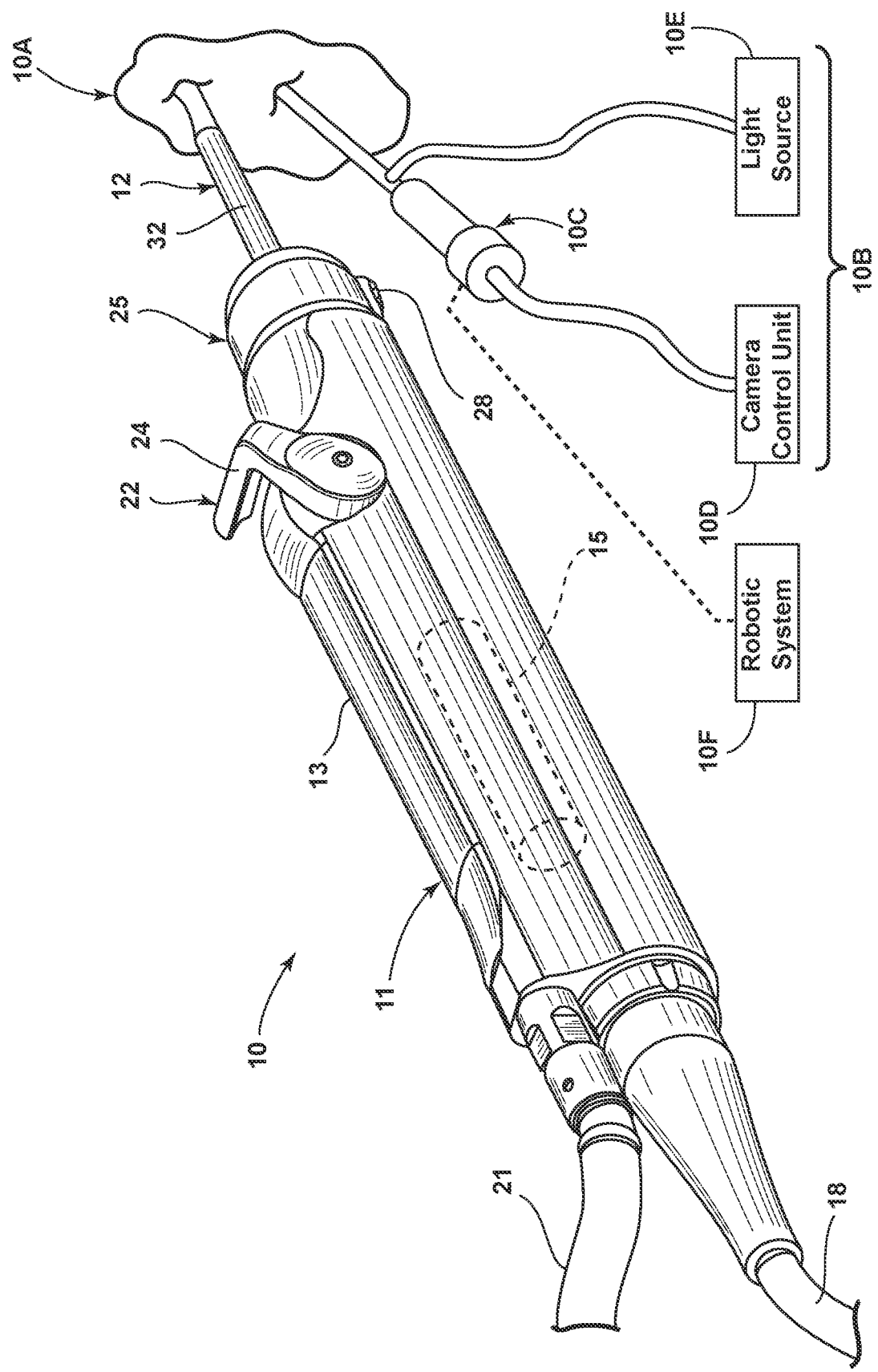
FIG. 1 is a perspective view of a surgical tool system, including a handpiece with a multi-functional surgical accessory attached thereto according to an embodiment.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the system and designated parts thereof. The words "forwardly" and "distally" will refer to the direction toward the end of the system which is closest to the patient, and the words "rearwardly" and "proximally" will refer to the direction toward the end of the system which is furthest from the patient. Said terminology will include the words specifically mentioned, derivatives thereof, and words of similar import.

DETAILED DESCRIPTION

Reference will now be made in detail to implementations and embodiments of various aspects and variations of the invention, examples of which are illustrated in the accompanying drawings. Although variations of the systems, methods, uses and kits are described, other variations of the systems, methods, uses and kits may include aspects of the systems, methods, uses and kits described herein combined in any suitable manner having combinations of all or some of the aspects described.

Figure 2:
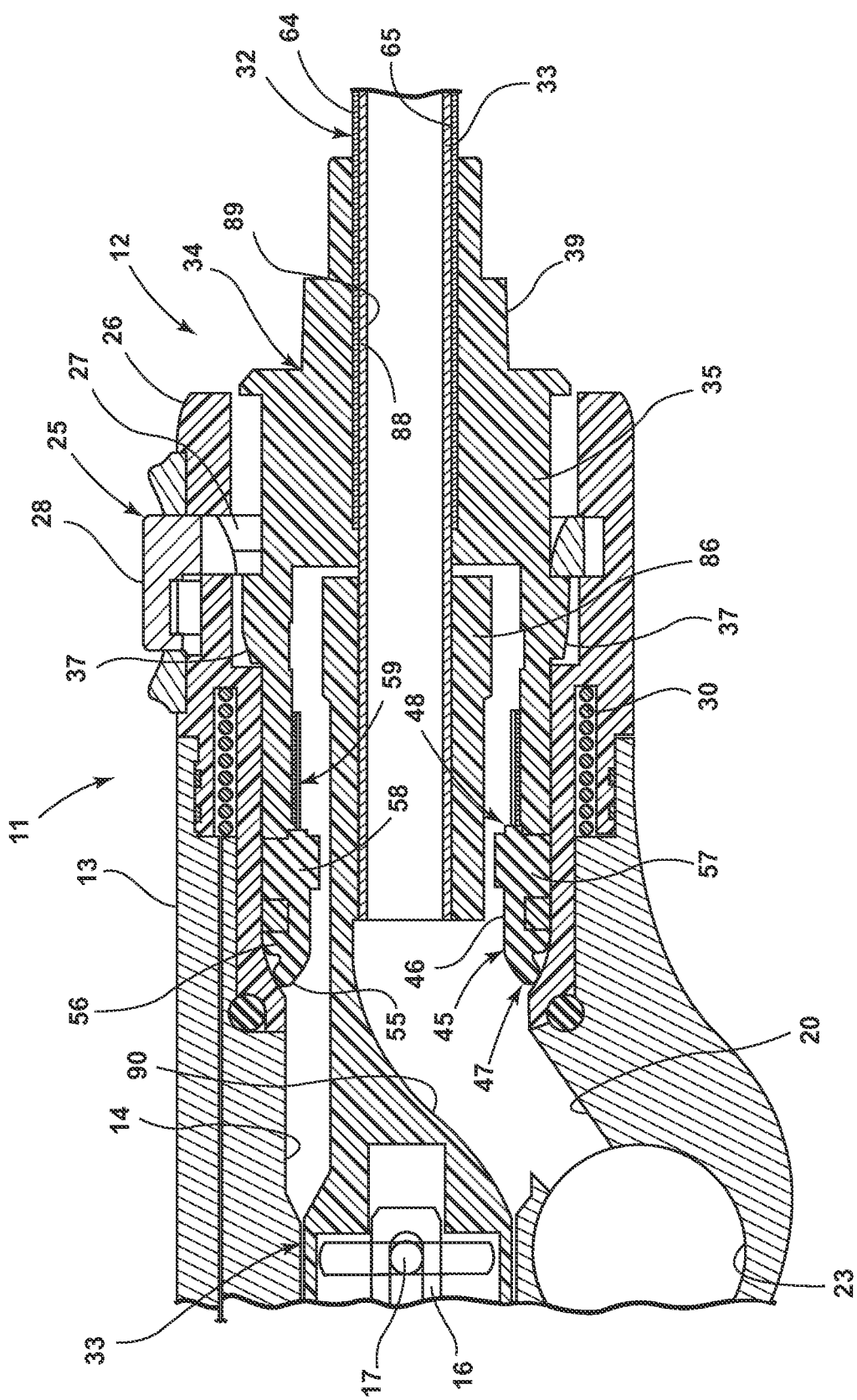
FIG. 2 is an enlarged, fragmentary, longitudinal and cross-sectional view of the handpiece of FIG. 1 with a surgical accessory attached thereto.

Referring to FIGS. 1 and 2, an exemplary surgical tool system 10 for manipulating tissue at a surgical site 10A is illustrated. The system 10 includes a handpiece 11, which at its distal end mounts thereon (or couples thereto) a multi-functional surgical accessory 12 for cutting or resecting tissue. The tool system 10 may be utilized with a medical imaging system 10B. The medical imaging system 10B may include an endoscopic camera 10C, a camera control unit 10D for controlling the camera 10C and a light source 10E which cooperates with the camera 10C to provide light to the surgical site 10A. Further, an image or video obtained by the endoscopic camera 10C may be displayed on a monitor (not shown) for use by the surgeon. The tool system 10 may also be utilized with a robotic system 10F, which system 10F may in some embodiments include a robotic arm which can be used to hold and/or manipulate the endoscopic camera 10C.

The handpiece 11 may be a commercially available surgical handpiece. For example, the handpiece 11 may be a handpiece manufactured by the assignee hereof, under Model Nos. 375-704-500, 375-701-500 and 375-708-500, and is accordingly only briefly described herein. For example, the handpiece 11 includes an elongate outer housing 13 defining an elongate bore 14 therein. A motor 15 (shown diagrammatically only in FIG. 1) is disposed within the housing bore 14. The motor 15 includes an output or drive shaft 16, which drive shaft 16 mounts a drive pin 17 at the distal end thereof. A power cable 18 is coupled to the proximal end of the handpiece 11 for supplying power to the motor 15.

In the example in FIG. 1, the handpiece housing 13 defines therein an elongate suction bore (not shown) extending generally parallel to and sidewardly of the housing bore 14. This suction bore communicates with a diagonally extending suction passage 20 defined in the housing 13, which passage 20 provides communication between the distal end of the housing bore 14 and the suction bore. Suction is drawn through the handpiece 11 by a suction pump (not shown), which is connected to the handpiece 11 via a suction tube 21. Suction flow through the handpiece 11 is regulated by an adjustable valve 22 having a valve stem (not shown) which is movably mounted in a valve bore 23 defined in the housing 13. The valve 22 is adjusted by the user via a movable handle or arm 24 connected to the valve stem.

The surgical accessory 12 is removably attachable to the distal end of the handpiece 11 by, for example, a coupler such as a coupling assembly 25 in the example in FIG. 1 which is provided on the handpiece 11. The coupling assembly 25 in the example in FIG. 1 may include, for example, as is illustrated in FIG. 2, a generally ring-shaped collet 26 secured to the distal end of the handpiece housing 13. A locking ring 27 is movably disposed in the collet 26 and is biased to hold the surgical accessory 12 within the housing bore 14 of the handpiece 11. A release button 28 is provided on the locking ring 27, and is used to release the locking ring 27 and allow removal of the surgical accessory 12 from the handpiece 11. Further, a coil 30 is provided in the collet 26, which is used to facilitate inductive signal transfer to/from a radio-frequency identification device (RFID) disposed in the surgical accessory 12 as discussed below.

Figure 3:
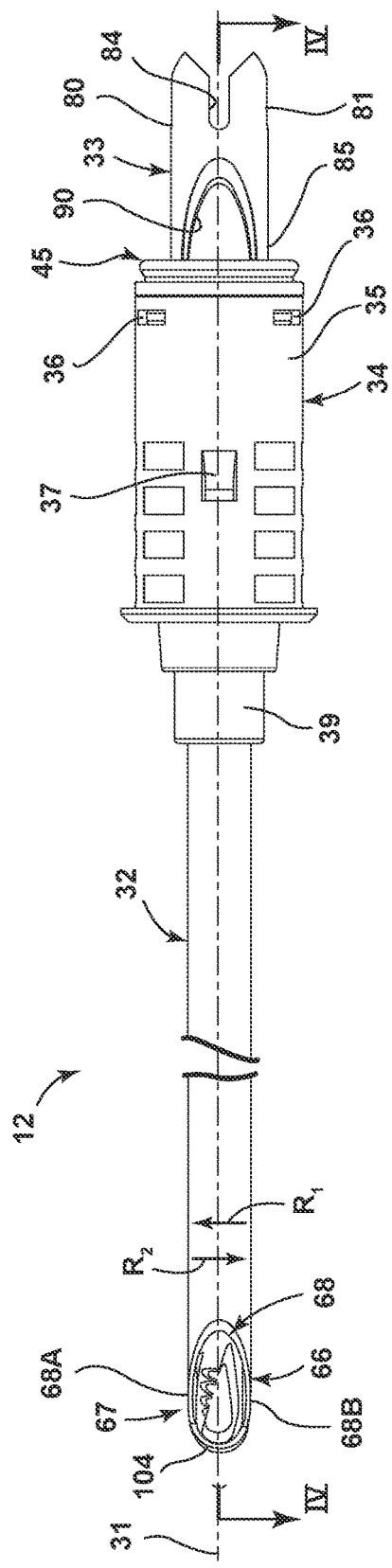
FIG. 3 is an enlarged and fragmentary view of the surgical accessory.
Figure 4:
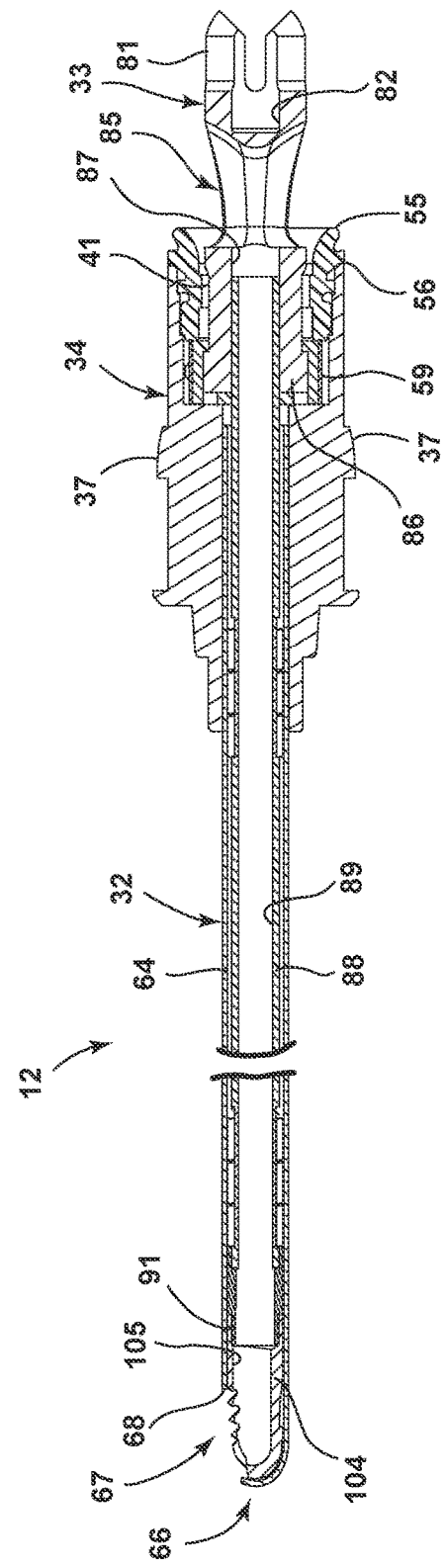
FIG. 4 is an enlarged longitudinal cross-sectional view of the surgical accessory of FIG. 3, as seen generally along line IV-IV in FIG. 3.

Referring to FIGS. 2-4, the surgical accessory 12 will now be described according to the various embodiments. The surgical accessory 12 is configured as a multi-functional device in that same incorporates multiple tissue-treating areas in a single device, one of which areas can be used to carry out hard tissue removal, resection or cutting such as the removal of cortical bone, cancellous bone or cartilage, and the other of which areas can be used to carry out soft-tissue removal, resection or cutting such as the removal, resection or cutting of soft connective tissue including, for example, ligaments, tendons or muscle. Examples of various implementations which can be used to provide such functionality for a surgical accessory are described below.

In the embodiment illustrated in FIGS. 2-4, the surgical accessory 12 defines a central longitudinal axis 31 (FIG. 3), and includes an outer cannula or tubular housing element 32 and a tubular cutting element 33 disposed within the housing element 32. The housing element 32 includes a hub 34 which defines the proximal end thereof. The hub 34 is defined by a generally tubular base body 35, which defines therein a pair of generally rectangular and diametrically-opposed openings 36 adjacent the proximal end thereof. The base body 35 also has formed thereon a pair of outwardly-projecting, diametrically opposed and generally ramp-shaped ears 37 disposed distally of the openings 36. The ears 37 cooperate with the coupling assembly 25 of the handpiece 11 to secure the accessory 12 therein. The hub 34 has a distal end defined by a head 39 or nose of a reduced diameter as compared to the base body 35. Further, the hub 34 defines therein a bore 41 which extends completely through the hub 34, and with which the openings 36 of the base body 35 communicate.

In the embodiment illustrated in FIGS. 2-4, an annular seal 45 is disposed within the proximal end of the bore 41 of the hub 34. The seal 45 is constructed of a resilient elastomeric material, and is defined by a main section 46 and axially-spaced proximal and distal sections 47 and 48 disposed at respective opposite ends of the main section 46. The proximal section 47 defines thereon a pair of annular ribs 55 and 56, which are disposed in sealing engagement with an inner annular surface of the collet 26 of the handpiece 11 when the accessory 12 is coupled thereto, as shown in FIG. 2. The distal section 48 defines thereon a pair of outwardly projecting and diametrically-opposed lock tabs 57 which engage within the respective openings 36 of the hub 34 to secure the seal 45 to the hub 34 and fix the axial position of the seal 45 relative thereto. The distal section 48 additionally defines thereon a pair of inwardly projecting and diametrically-opposed stop tabs 58, which are generally radially aligned with the respective lock tabs 57. As shown in FIGS. 2 and 4, an RFID device 59 encapsulated within a ring structure is located within the hub bore 41 distally from, and in axially-adjacent relationship with, the distal section 48 of the seal 45.

The housing element 32 (FIGS. 2-4) additionally includes an elongate housing tube 64 which projects distally from the hub 34. More specifically, the housing tube 64 has a proximal end which is fixedly mounted within the distal portion of the bore 41 of the hub 34. The housing tube 64 defines an elongate bore or conduit 65 therein, in which the cutting element 33 is disposed as discussed below. Referring to FIGS. 3 and 4, the housing tube 64 has a distal end 66 which in the illustrated embodiment is cut so as to define a window 67 having an annular edge 68, which window 67 in the illustrated embodiment opens both sidewardly and distally of the tube 64. The annular edge 68 includes a pair of cutting edges 68A and 68B oriented in substantially opposed relation with one another and which are spaced circumferentially (or sidewardly-spaced) from one another along the distal end 66 of the housing tube 64. The annular edge 68, with its cutting edges 68A and 68B, is formed as a result of a cutting operation performed on the distal end 66 of the housing tube 64, and thus these edges effectively define free and circumferentially extending terminal edges of the housing tube 64 so as to form the window 67.

Turning now to the cutting or resecting element 33, same includes a hub 80 which defines the proximal end thereof. The hub 80 incorporates a motor-engaging drive element 81 defining a proximally opening bore 82, and a slot 84 which extends transversely to the longitudinal axis of the cutting element 33. The hub 80 additionally includes a neck 85 which projects distally from the drive element 81. The neck 85 terminates at a head 86 which has an enlarged outer diameter. In this regard, the outer diameter of the head 86 is slightly larger than the inward projection of the respective stop tabs 58 of the seal 45. A bore 87 extends through the neck 85 and the head 86, in which an elongate and tubular drive shaft 88 is fixed. In this embodiment, the drive shaft 88 defines therein a suction passage 89 which is in communication with a suction port 90 defined in the neck 85, which suction port 90 is in turn in communication with the suction passage 20 of the handpiece 11.

The drive shaft 88 has a distal end 91 which mounts a cutting head 104 thereon. In the illustrated embodiment, the drive shaft 88 and the cutting head 104 are constructed as separate components which are fixed to one another. In this regard, the drive shaft 88 may be constructed of a rigid plastic and then induction welded to the cutting head 104, which may be constructed of rigid metal, such as stainless steel. Alternatively, the drive shaft 88 and the cutting head 104 may be constructed as an integral or one-piece member formed from rigid metal, such as stainless steel. The cutting head 104 is substantially cylindrical and tubular in the illustrated embodiment, and defines a hollow interior 105 which extends along substantially the entire longitudinal extent of the cutting head 104 and in this embodiment communicates with the suction passage 89 of the drive shaft 88. It will be appreciated that the drive shaft 88 need not be hollow as shown, and instead may be provided as a solid member which may be rigid or flexible, as discussed further below.

Figure 8:
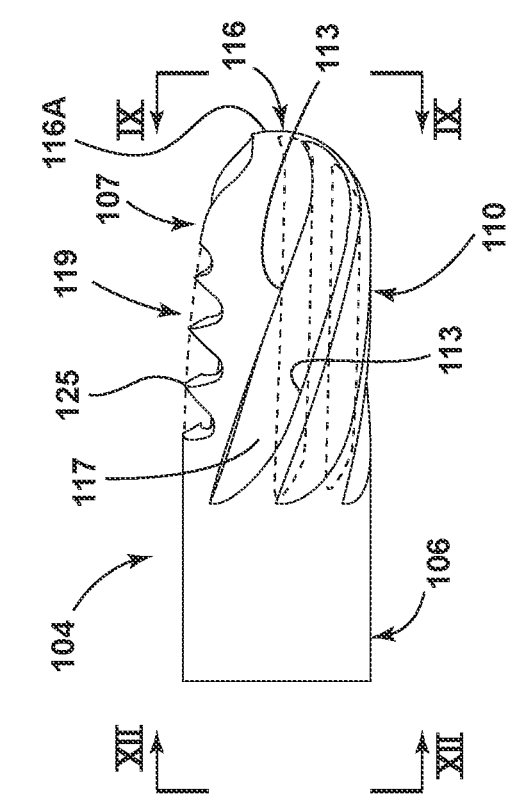
FIG. 8 is a cross-sectional view as seen generally along line VIII-VIII in FIG. 5.

As shown in detail in the embodiment in FIG. 8, the cutting or resecting head 104 includes a substantially tubular or substantially cylindrical wall 108 with a tubular proximal end portion 106 of a generally constant diameter and a distal end portion 107 connected to and extending distally from the proximal end portion 106. The wall 108 has an exterior surface 109 extending both circumferentially and axially, and an interior surface 111 facing opposite the exterior surface 109 and defining the interior 105 of the cutting head 104. The cutting head 104, and particularly the distal end portion 107 thereof, is provided with different and distinct types of tissue-treating areas, which areas may be utilized to carry out tissue removal, tissue-cutting or tissue-resection, which areas are spaced from one another along the circumference of the cutting head 104. In this embodiment, these areas are located on opposite sides of the cutting head 104.

Figure 7:
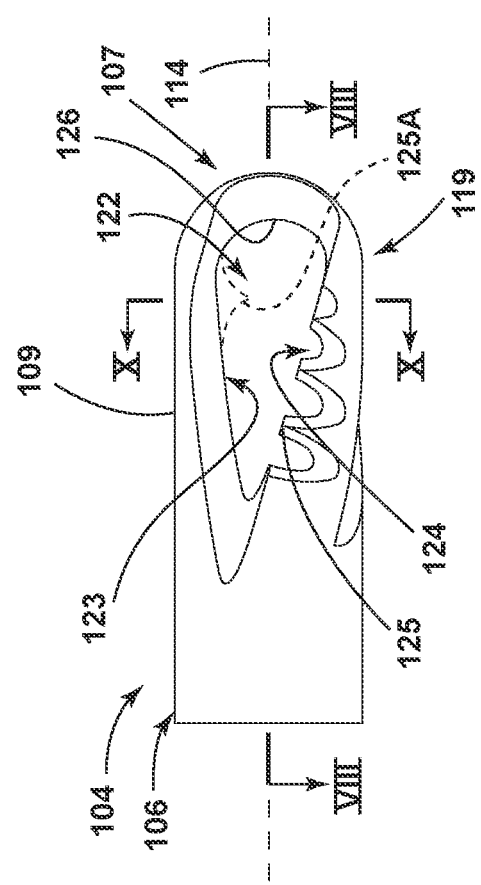
FIG. 7 is an enlarged and isolated view of the cutting head of the surgical accessory rotated approximately 180 degrees from the position shown in FIG. 5.
Figure 6:
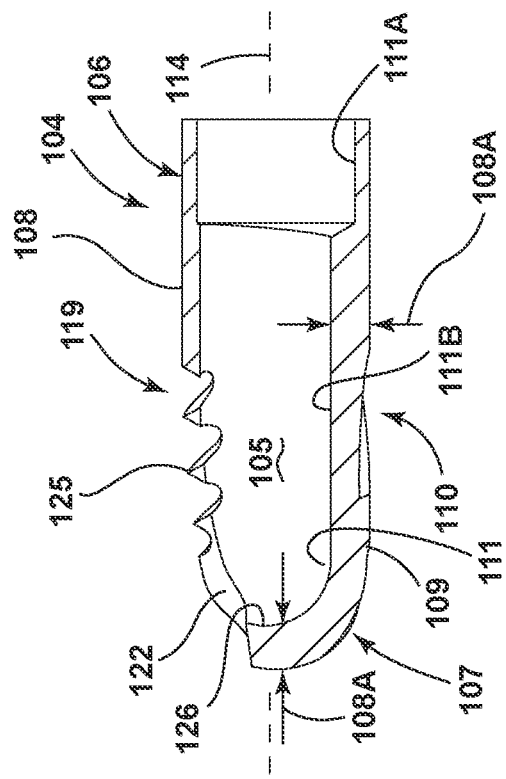
FIG. 6 is an enlarged and isolated view of the cutting head of the surgical accessory, rotated approximately 90 degrees from the position shown in FIG. 5.
Figure 9:
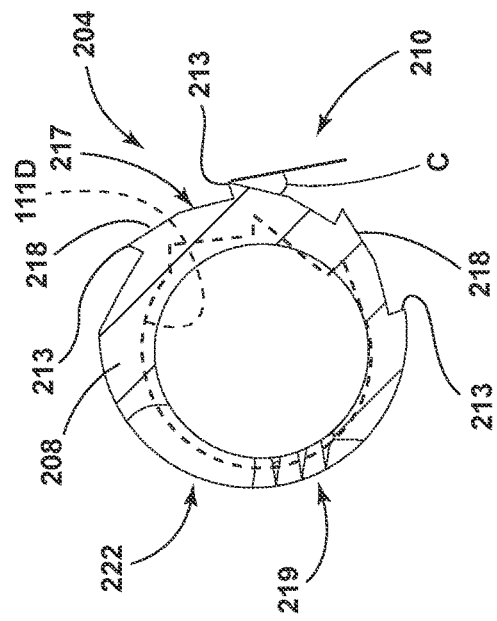
FIG. 9 is an enlarged distal end view as seen along line IX-IX in FIG. 6.

As shown in the embodiment in FIG. 7, a first of these tissue-treating areas 110 is a circumferentially-extending abrading surface or region, which in this embodiment has a bur configuration incorporating a fluted region which in this embodiment includes a plurality of cutting surfaces 115 and flutes 117 oriented in an alternating manner with one another along part of the circumference of the cutting head 104. The cutting surfaces 115 and flutes 117 in this embodiment extend in a helical manner about the axis 114 and in a generally parallel manner with one another along a majority of the longitudinal extent of the distal end portion 107. Each cutting surface 115 terminates at a cutting edge 113 which defines the radially outermost extent thereof. The terminal cutting edges 113 extend gradually towards one another in the proximal to distal direction and terminate adjacent a tip 116 of the distal end portion 107, as best shown in FIGS. 6 and 9. In the illustrated embodiment, the terminal edges 113 stop proximally of the tip 116, which effectively creates a bearing surface 116A at the tip 116. Such a bearing surface provides a support surface which cooperates with an adjacent interior surface of the distal end 66 of the housing tube 64 to support the cutting element 33 during movement relative to the housing element 32 as discussed below. It will be appreciated that the cutting surfaces 115 and the flutes 117 may alternatively be non-helical or substantially straight or linear so as to extend generally parallel with the axis 114 as shown in dotted lines in FIG. 6, or so as to be oriented at an angle relative to the axis 114.

In this embodiment, the first tissue-treating area 110 extends along a substantial circumferential portion of the exterior surface 109 of the cutting head 104, and the portion of the wall 104 on which the first tissue-treating area 110 is formed is solid and does not include any windows or openings which communicate with the interior 105 of the cutting head 104.

Figure 10:
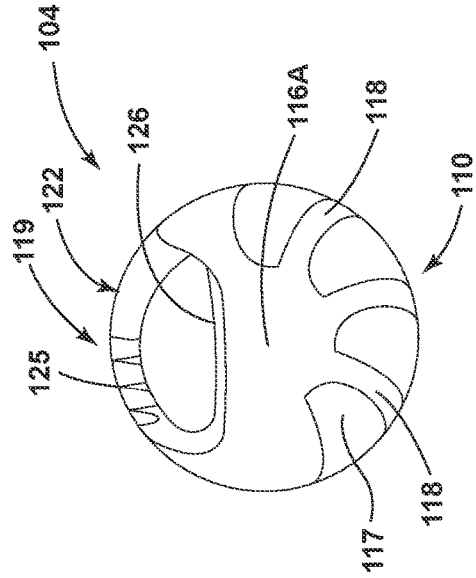
FIG. 10 is an enlarged cross-sectional view as seen generally along line X-X in FIG. 5.

In the illustrated embodiment and with reference to FIG. 10, on the side of the cutting head 104 on which the first tissue-treating area 110 is provided, the portions of the wall 108 located between neighboring pairs of cutting surfaces 115 (which portions define the respective flutes 117) are provided with lands 118. More specifically, the flute 117 of the cutting head 104 is formed so as to leave remaining a land 118 between adjacent pairs of cutting surfaces 115. As such, in the illustrated embodiment, the land 118 has a contour which corresponds with the curvature of the exterior surface 109 of the cutting head 104. As shown in FIGS. 7, 9 and 10, each land 118, in addition to extending a short distance circumferentially along the cutting head 104, also extends substantially longitudinally along the cutting head 104, and follows the contour of the helix of the cutting surfaces 115 and flutes 117. In one embodiment, the lands 118 have a circumferential dimension, based on a cutting head 104 with a 5.5 mm diameter, of approximately 0.020 inch. In another embodiment, for a cutting head 104 with a 4.0 mm diameter, the circumferential dimension of the lands 118 is approximately 0.010 inch. In other embodiments, the circumferential dimension for these sizes of cutting heads 104 may be in the range of 0.005-0.040 inch. The lands 118 serve to minimize wear on the interior surface of the housing tube 64 of the outer housing element 32 during operation of the surgical accessory 12, as discussed in further detail below.

Figure 5:
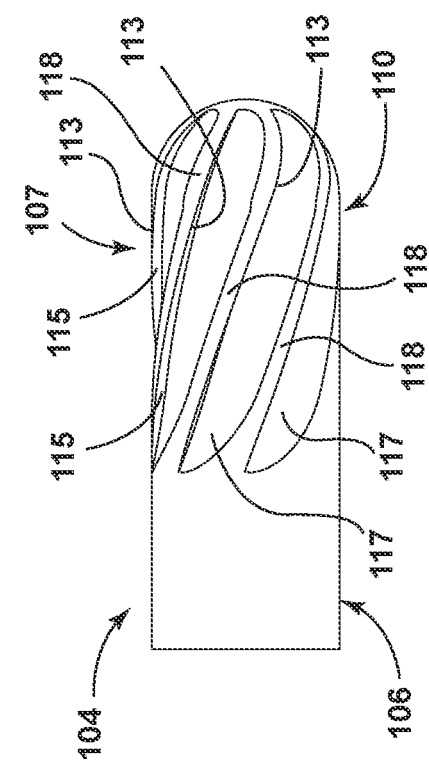
FIG. 5 is an enlarged and isolated view of an embodiment of the cutting head of the surgical accessory.

The cutting head 104, on a region thereof circumferentially-spaced from the first tissue-treating area 110, is provided with a second tissue-treating area 119 having a windowed configuration as shown in the embodiment in FIGS. 5 and 6. In this embodiment, the area 110 is located substantially diametrically opposite the area 119. Further, the area 119 is non-fluted. In this regard, the wall 108 at the distal end portion 107 of the cutting head 104 is cut to define a window 122, which window 122 is formed as an elongated opening in the cutting head 104. In the illustrated embodiment, the window 122 opens primarily sidewardly or transversely relative to the axis 114 and communicates with the interior 105 of the cutting head 104. One side of the window 122 defines a first cutting edge 123, which cutting edge 123 is smooth and substantially linear. Further, and with reference to FIG. 5, the edge 123 in the illustrated embodiment angles inwardly as same extends longitudinally along the cutting head 104 in a distal to proximal direction. The opposite side of the window 122, disposed in substantially facing and opposed relation with the first cutting edge 123, defines a second cutting edge 124 which in this embodiment is provided with at least one, and here a plurality, of teeth 125. In the illustrated embodiment, the teeth 125 are of gradually increasing depth (wherein the depth is considered to encompass the distance from the root or base of the tooth 125 to the tip thereof) as the teeth 125 progress in the distal to proximal direction. Additionally, the terminal outer ends of the teeth 125 may be aligned with one another as shown so that same substantially follow the helical angle of the cutting surfaces 115 and flutes 117. It will be appreciated that the configuration of the teeth 125 as shown is an example of only one type of tooth configuration, and other tooth configurations are usable. In this regard, other applicable tooth configurations may include a lesser or greater number of teeth than that shown. Further, the tooth depths may be constant or substantially equal to one another. Additionally, the placement of the teeth along the cutting edge 124 may differ from that shown, in that the teeth may be spaced a greater or lesser distance from one another. Further, the cutting edge 124 may instead be non-toothed such that the edge 124 is angled in the manner shown in FIG. 5, but instead has a smooth edge in place of the teeth 125 as shown in dotted lines in the embodiment in FIG. 6. Additionally, the cutting edge 123 may include one or more teeth 125A as shown in dotted lines in FIG. 5.

As best shown in FIGS. 5 and 9, the window 122 additionally includes a distal cutting edge 126, which in the illustrated embodiment is arcuate and extends between and interconnects the opposed first and second cutting edges 123 and 124.

It will be appreciated that the cutting window 122 may be provided with various geometries based on the type of cutting action the cutting head 104 is intended to carry out. For example, the teeth 125, 125A of the cutting edge 124 may be provided with an internal shear angle in order to achieve the desired cutting action. In this regard, "shear angle" in this context is intended to refer to the opening angle of the window 122 which is determined during the cutting process which forms the window. For example, the teeth may be provided with a negative internal shear angle which less than zero degrees, a positive internal shear angle which is greater than zero degrees, or a zero degree shear angle. Further, the teeth may be provided with no shear angle, meaning that the internal cutting face of the tooth is oriented in a plane which intersects the central axis 114 of the cutting head 104. The opposite cutting edge 123 and/or the proximal cutting edge 126 may also be provided with the various geometries discussed above, if desirable or necessary.

Referring to FIGS. 8 and 10, the cylindrical wall 108 of the cutting head 104 has a thickness dimension 108A, as defined between the exterior surface 109 and the interior surface 111 thereof, which is greater in the area of the first tissue-treating area 110 as compared to the wall thickness of the wall 108 on the side or in the region of the second tissue treating area 119. More specifically, the wall 108, as same extends circumferentially about the cutting head 104, gradually lessens in its thickness dimension as same approaches the cutting edges 123 and 124 of the second tissue-treating area 119. Additionally, the wall 108 has the thickness dimension 108A from adjacent the proximal origination point of the edges 113 up to the distal cutting edge 126.

This increased wall thickness 108A of the wall 108 in the area of the first tissue-treating area 110 provides the cutting head 104 with increased rigidity and structural integrity in this area to permit the formation, for example by machining, of the cutting surfaces 115, the flutes 117 and the lands 118 of the area 110. As shown in FIGS. 8, 10 and 12, the interior surface 111, in the area of the proximal end 106 of the cutting head 104, defines a first bore 111A which is centered on the central axis 114 of the cutting head 104 to allow attachment of the cutting head 104 to the drive shaft 88 of the surgical accessory 12. In the area of the tissue-treating areas 110 and 119, the interior surface 111 defines a second bore 111B disposed axially adjacent and distally of the first bore 111A, which second bore 111B has a central axis 114A radially offset from the central axis 114 to provide the increased wall thickness of the wall 108 adjacent the first tissue-treating area 110 as discussed above. This offset bore configuration, and specifically the formation of the second bore 111B with its axis 114A offset from the central axis 114 of the cutting head 104, allows the formation of a larger space within the cutting head 104 for evacuating surgical debris from the surgical site after same enters the window 122, and at the same time provides a greater wall thickness in the area of the bur-type first tissue-treating area 110. The second bore 111B as discussed above has a circular cross-section. Alternatively, and as shown in dotted lines in FIG. 10, the second bore, indicated with reference number 111C, may have a non-circular configuration, such as an elongated or oval configuration with its axis aligned with axis 114 or offset therefrom. In this embodiment, the radial distance between the dotted line which represents the bore 111C and the base of each of the flutes 117 of the first tissue-treating area 110 is substantially the same, which provides sufficient thickness and strength to the wall 108 in the area of the first tissue-treating area 110. However, the area of the non-circular second bore 111C is greater than the area of the circular second bore 111B, which maximizes the suction area for removing debris. The second bore may also have other configurations, such as a D-shaped configuration, with the straight part of the D-shape being located circumferentially adjacent the first tissue-treating area 110 in order to provide sufficient material thickness in this area as discussed above. Still further, the second bore may have a configuration 111D such as that shown in dotted lines in FIG. 11, wherein parts of the second bore adjacent the first tissue-treating area copy or substantially follow the geometry thereof, in order to maximize both the thickness of the wall and the cross-sectional area of the suction path. Alternatively to providing two bores within the cutting head 104 as discussed above, it is also possible to provide a single bore of a constant diameter through the cutting head 104, which single bore is of a diameter small enough to allow both a cutting window and flutes to be formed on the cutting head 104.

The above-described configuration of the wall 108 of the cutting head 104 of the surgical accessory 12 allows the cutting head 104 to include both a hard-tissue abrading region, such as the first tissue-treating area 110, and a soft-tissue removing region, such as the second tissue-treating area 119, on a single cutting head 104. The circumferential surface region of the cutting head 104 which is occupied by the first tissue-treating area 110 should be chosen so that a maximum number of flutes 117 can be provided to achieve efficient hard-tissue removal. In this regard, in one embodiment, the first tissue-treating area 110 occupies approximately 180 degrees or half of the circumference of the cutting head 104. In other embodiments, the first tissue-treating area 110 may occupy between 45-270 degrees of the circumference of the cutting head 104.

Figure 11:
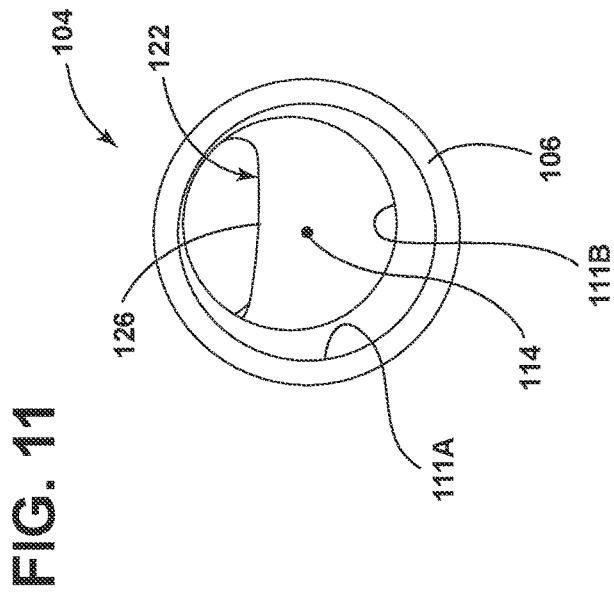
FIG. 11 is an enlarged cross-sectional view similar to that shown in FIG. 10, but illustrating a variation of the cutting head including relief angles.
Figure 12:
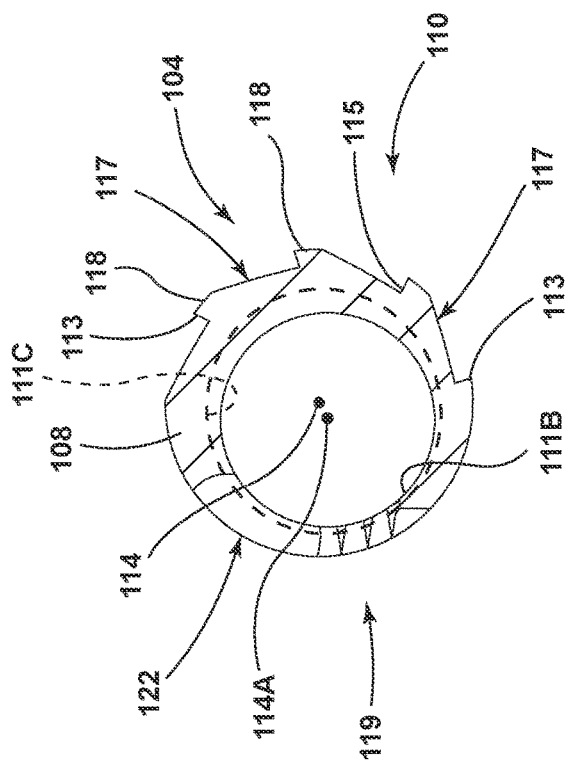
FIG. 12 is an enlarged proximal end view as seen along line XII-XII in FIG. 6.

FIG. 11 is a transverse cross-sectional view of a variation of the cutting head 104 discussed above. Components of this variation which are similar or identical to components of the first-described embodiment will include the same reference numbers plus "100", and a detailed description of all components will accordingly not be provided. In accordance with this variation, the cutting head 204, in the area of the first tissue-treating area 210, is provided with relief angles C. More specifically, a relief angle C is cut into the wall 208 of the cutting head 204 between neighboring pairs of cutting surfaces 215, which relief angle C results in the formation of a flat 218. Each flat 218 originates at a respective terminal edge 213 of a cutting surface 215 and extends in a circumferential direction away therefrom and towards the adjacent next cutting surface 215. Providing the cutting head 204 with relief angles C results in sharper terminal edges 213, which allows more aggressive tissue removal from a surgical site.

The cutting element 33 is assembled to the outer tubular housing element 32 by inserting the distal end 91 of drive shaft 88 of the cutting element 33 into the bore 41 at the proximal end of hub 34. During this insertion, the enlarged head 86 of the hub 80 expands the seal 45 and the head 86 pushes past the stop tabs 58, at which point the seal 45 essentially resumes its original shape. The stop tabs 58, while allowing some axial displacement of the cutting element 33 relative to the housing element 32, prevent the cutting element 33 from detaching or falling out of the housing element 32 due to gravitational forces.

The assembled surgical accessory 12 is secured to the handpiece 11 by inserting the hubs 34 and 80 into the open distal end of the collet 26. The ears 37 of the hub 34 seat within the collet 26, and the locking ring 27 serves to hold the surgical accessory 12 within the handpiece 11. The above securement of the surgical accessory 12 to the handpiece 11 causes the drive element 81 to engage the motor output shaft 16. More specifically, the drive pin 17 of the output shaft 16 seats within the slot 84 of the drive element 81, such that the rotational movement of the output shaft 16 is transferred to the cutting element 33. It will be appreciated that the handpiece 11 and the coupling arrangement thereof which cooperates with the surgical accessory 12 as described above is only an example of one type of handpiece which may be utilized with the surgical accessory 12. In this regard, the surgical accessory may be configured to cooperate with other types of handpieces which handpieces may incorporate alternative arrangements for purposes of coupling to the surgical accessory. For example, a chuck-type coupling arrangement can be utilized to fixedly attach the surgical accessory 12 to the handpiece. Other types of coupling arrangements may be utilized, provided that same maintain the outer housing element 32 non-rotatable relative to the handpiece and provide an appropriate driving engagement of the cutting element 33.

In operation, the distal end of the surgical tool system 10 is inserted into the surgical site 10A. The cutting element 33 is controlled by a control unit (not shown) connected to the handpiece cable 18, which control unit supplies electrical power to the motor 15 of the handpiece 11 in order to actuate the cutting element 33 and control the rotational speed thereof. If cutting of tissue is desired, then the motor 15 is activated so as to cause the cutting element 33 to rotate within and relative to the outer housing element 32. In this regard, it will be appreciated that the control unit may include appropriate controls (e.g., control buttons) so as to allow the surgeon or operator to select the desired operations for the surgical accessory 12. These control functions of the cutting element 33 may alternatively be performed directly from the handpiece 11 which would then include the appropriate control buttons thereon. Alternatively, the control unit may be associated with a switch, either through a suitable cable or wirelessly, to allow the surgeon to operate the controls remotely. Such a switch may be a footswitch or a hand switch.

As shown in FIGS. 3 and 4, with the cutting element 33 disposed within the housing element 32 and the accessory 12 secured to the handpiece 11 as described above, the cutting head 104 is positioned axially adjacent the window 67 of the housing element 32 so that at least a portion of the cutting head 104 is exposed through the window 67. In this assembled configuration of the cutting element 33 and housing element 32, the edges 123 and 124 are disposed radially closely adjacent to the interior surface of the housing element 32, so that the edges 123 and 124 are in a position to cooperate with the edges 68A and 68B of the housing element 32. During rotation of the cutting element 33 within and relative to the housing element 32, the bearing surface 116A at the tip 116 of the cutting head 104 and the lands 118 provided on the cutting head 104 in the embodiment of FIG. 10 serve as support surfaces which cooperate with the respective adjacent interior surfaces of the distal end 66 of the housing tube 64. The bearing surface 116A and the lands 118 assist in minimizing or at least reducing vibration of the cutting element 33 relative to the housing element 32, and also assist in minimizing or at least reducing particle generation during movement of the cutting element 33 relative to the housing element 32. In this regard, the lands 118 are particularly effective in reducing particle generation when a lateral or transverse force is applied to the surgical accessory 12 during a hard-tissue removal operation as discussed further below. These features which achieve reduction of vibration and particle generation serve to minimize wear of the components while ensuring good cutting or resecting performance, as discussed further below. In the variation of FIG. 11, no such bearing areas are provided due to the provision of the relief angles C which form the flats 218, as this variation is intended to provide a more aggressive cutting action. In this regard, in the embodiment of FIG. 10 which includes the lands 118, the relief angle is essentially zero degrees, meaning that the portion of the land 118 immediately circumferentially adjacent the terminal edge 113 of the adjacent cutting surface 115 corresponds to a tangent of the outer curved surface of the cutting head 104 immediately adjacent a terminal edge 113 thereof. In the embodiment of FIG. 11, the cutting head 104 is provided with relief angles C resulting in the respective flats 218. The relief angle C may have a value in the range of zero degrees, which corresponds to the embodiment of FIG. 10 and results in the formation of lands 118, upwards to about forty degrees, which results in the formation of straight areas or flats 218 as shown in FIG. 11. One preferred range of the relief angle C is zero degrees to twenty degrees.

As shown in FIG. 3, with the cutting element 33 disposed within the housing element 32 and the surgical accessory 12 secured to the handpiece 11, the surgical accessory 12 can be operated to remove hard and soft tissue in various modes of operation, based on surgeon preference and/or the type of surgery which is being carried out. According to one method of operation, the surgical accessory 12 may be operated first in an oscillating mode and thereafter may be operated in a continuous mode. For example, when the cutting element 33 is operated in the oscillating mode, the cutting element 33 is rotated a specified number of 360 degree cycles in a forward direction R1, before reversing and rotating a specified number of 360 degree cycles in an opposite or reverse direction R2. This oscillating mode of the surgical accessory 12 is useful in preparing the targeted area for a hard-tissue removal, resection or cutting operation by first removing, resecting or cutting soft tissue from the targeted area. More specifically, when the cutting element 33 is rotated by the handpiece motor 15 in the forward direction R1, the edge 123 of the window 122 of the second tissue-treating area 119 of the cutting element 33 moves towards or approaches the edge 68A of the housing window 67, and soft tissue is cut by the scissoring action between the opposed edges 123 and 68A as the window closes 67 due to continued rotation of the cutting element 33 in direction R1. After the cutting element 33 has rotated through the specified number of cycles in the forward direction R1, the cutting element 33 changes direction and rotates in the reverse direction R2. When the cutting element 33 is rotated in the reverse direction R2, the edge 124 of the window 122 of the second tissue-treating area 119 of the cutting element 33 moves towards or approaches the edge 68B of the housing window 67 and the tooth or teeth 125 of the edge 124 grab and pull soft or fibrous tissue into the housing tube window 67 and towards the edge 68B thereof. This tissue is cut by the scissoring action between the tooth or teeth 125 and the opposed edge 68B of the housing tube window 67 as same closes due to continued rotation of the cutting element 33 in direction R2.

After completion of the oscillating mode of the surgical accessory 12 as described above, same may then be operated in the continuous mode. In this mode, the cutting element is rotated through continuous 360 degree cycles in the forward direction R1 at a relatively high speed in order to remove or resect hard tissue. More specifically, as the cutting element 33 rotates in the direction R1, the first tissue-treating area 110 approaches and eventually aligns with the housing window 67, and when the area 110 is exposed through the window 67, then hard tissue is resected by the area 110. After this continuous mode of operation where the cutting element 33 is rotated in direction R1 is carried out, it may be preferable to rotate the cutting element 33 in direction R2 to provide a finishing or polishing operation on the targeted tissue.

In some types of surgery, it may be desirable to initially operate the surgical accessory 12 in a continuous and relatively high-speed forward mode (direction R1) so as to clear the targeted site of soft tissue in order to expose the hard tissue or bone for an abrading operation. In this mode, the cutting element 33 is rotated continuously in direction R1 at a high speed, which serves to tear off soft fibrous tissue and clear the site for an abrading operation. In some cases, this mode may be more effective for removing soft tissue as compared to the preparatory oscillating mode described above.

As discussed above, the edge 123 of the window 122 provided on the cutting head 104 may, in some embodiments, be provided with a tooth or teeth 125A. Providing teeth on both sides of the window 122 of the cutting head 104 in this manner may serve to improve soft-tissue resecting performance, for example when the surgical accessory 12 is operated in the oscillating mode described above. In this regard, the tooth 125A in this embodiment is of a larger size than the teeth 125 provided along the opposite cutting edge 124 so as to be capable of resecting hard or bony tissue or so to at least be capable of withstanding the impact of hard tissue thereon, since the tooth 125A is oriented in the hard-tissue resecting direction as determined by the configuration (for example, based on the rake direction) of the first tissue-treating area 110.

If desirable or necessary, suction can be provided at the surgical site by manipulating the valve 22 on the handpiece 11 to draw surgical debris from the surgical site through the rotationally aligned windows 67 and 122 of the outer housing element 32 and the cutting element 33, into the drive shaft suction passage 89, into the handpiece suction passage 20 and proximally through the handpiece 11 towards the suction pump.

The surgical accessory with the distal end which incorporates two differently configured types of tissue-treating areas as discussed in detail above achieves excellent resecting or cutting performance while minimizing wear. This may be achieved, at least in part, by providing the housing tube 64 of the housing element 32 with a greater hardness as compared to the cutting head 104, or by providing the cutting head 104 with a greater hardness as compared to the housing tube 64. For example, both the housing tube 64 and the cutting head 104 may both be constructed of surgical-grade or high-grade stainless steel and then both surface treated to increase the hardness thereof, with the housing tube 64 undergoing a surface-treatment which ultimately provides the housing tube 64 with a greater hardness than the cutting head 104. In one embodiment, the housing tube 64 may be constructed of Type 304 stainless steel which at a minimum is surface treated to approximately 860HV, and preferably to approximately 900+ HV. The cutting head 104 may be constructed of Type 440A stainless steel which at a minimum is surface treated to approximately 50 HRc, and preferably between approximately 50-55 HRC.

The surface-treating or hardening assists in preventing or at least minimizing flaking and/or particle generation due to the relative movement between the cutting element 33 and the inner surface of the housing tube 64. Additionally, the lands 118 provided on the cutting head 104 also serve to minimize particle generation which can occur during this relative movement. In this regard, in conventional bur-type surgical accessories, a bearing surface is typically provided on the cutting element proximally of the cutting head on which the bur is formed, which bearing surface serves to support the cutting element as same moves relative to the outer housing element and to compensate for transversely-oriented forces which may occur during use of the accessory. Further, it is desirable to provide a radial gap between the bur-type cutting head and the inner surface of the distal end of the outer housing element so as to prevent or at least minimize the generation of particles as a result of contact between the cutting head and the outer housing element. This type of contact can occur, for example, when the cutting head is brought into contact with hard or bony tissue and as a result a lateral or transverse force is applied to the surgical accessory as mentioned above. Conversely, in conventional shaver surgical accessories in which the cutting windows of the outer housing element and the inner cutting element cooperate with one another to sever tissue as the cutting element rotates relative to the outer housing element, it is desirable to provide a very minimal radial gap (a radial gap which is much less than the radial gap provided in a bur-type surgical accessory) between the distal ends of the inner cutting element and the outer housing element so as to ensure that the proper scissoring action between the windows occurs. Including both a hard-tissue treating area, such as a bur, and a soft-tissue treating area, such as a shaver-type window configuration, in a single surgical accessory was not believed possible prior to the development of the surgical accessory disclosed herein, due to concerns relating to particle generation and due to the substantially different radial gap requirements in the two types of surgical accessories as discussed above.

The surgical accessory 12 with its cutting head 104 which incorporates both a hard-tissue abrading area (first tissue-treating area 110) and a soft-tissue removing area (second tissue-treating area 119) maintains the small radial gap required to ensure proper cutting or scissoring action between the cooperating windows 122 and 67 of the cutting element 33 and the outer housing element 32, while at the same time prevents or at least minimizes particle generation and/or flaking by surface-treating or hardening the cutting element 33 and the outer housing element 32, and also by providing the lands 118 on the cutting head 104 at the first tissue-treating area 110, as discussed above.

Figure 14:
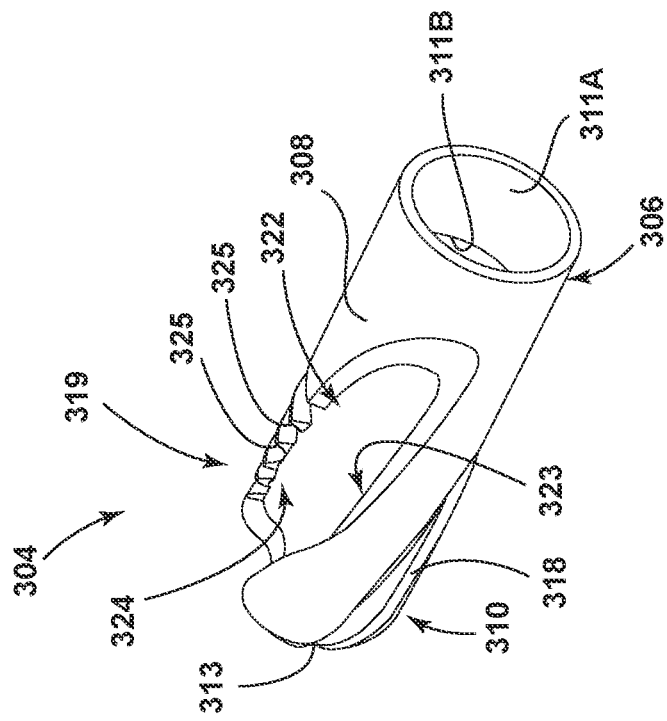
FIG. 14 is an enlarged perspective view of the cutting head of the surgical accessory shown in FIG. 13.
Figure 13:
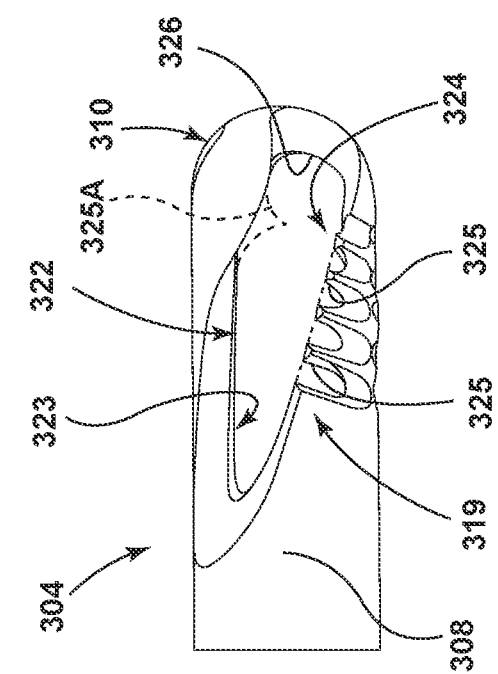
FIG. 13 is an enlarged and isolated view of another embodiment of the cutting head of the surgical accessory.

FIGS. 13 and 14 illustrate a further embodiment of the surgical accessory which will now be described. Components of this embodiment which are similar or identical to components of the first-discussed embodiment will include the same reference numbers plus "200", and a detailed description of all components will accordingly not be provided. As in the prior embodiment, the cutting head 304 is provided with two different types of tissue-treating areas. The first tissue-treating area 310 has an abrading surface or region configured as a bur, which is substantially identical to the first tissue-treating area 110 and will therefore not be described further. The second tissue-treating area 319 includes a window 322 with a substantially smooth first cutting edge 323 on one side thereof, and the opposite side of the window 322 disposed in substantially facing and opposed relation with the first cutting edge 323 defines a second cutting edge 324 which is provided with at least one, and here a plurality, of teeth 325. It will be appreciated that the first cutting edge 323 may be provided in one embodiment with a tooth 325A or teeth as shown in dotted lines in FIG. 13, and as discussed relative to the embodiment of FIG. 5. The window 322 is formed so as to substantially follow the helical angle of the cutting surfaces and flutes of the first tissue-treating area 310. The narrow size of the window 322 of this embodiment serves to minimize vibration of the cutting element 33 during use. Further, forming the window 322 so as to substantially follow the helix of the cutting surfaces and flutes allows a maximally-sized window for more efficient and effective tissue resection and removal. As in the prior embodiment, the wall thickness of the wall 308 of the cutting head 304 is of an increased dimension in the area of the first tissue-treating area 310. Additionally, this embodiment, depending on the intended use thereof, may be provided with lands 318 as shown in FIG. 14, or may alternatively be provided with relief angles and flats (not shown here but see FIG. 11) in order to increase the aggressiveness of the cutting head 304. Further, the second cutting edge 324 may alternatively be non-toothed such that same is helically-oriented but smooth, as shown in dotted lines in FIG. 13.

Figure 16:
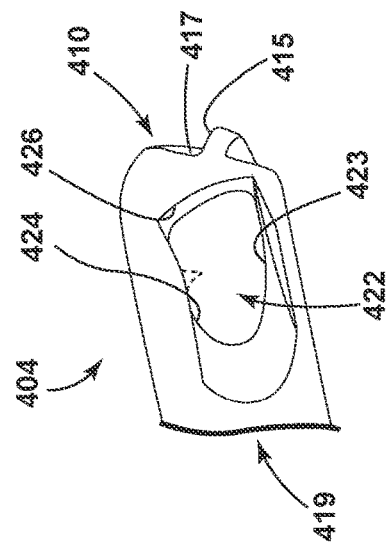
FIG. 16 is an enlarged and fragmentary perspective view of the cutting head of the surgical accessory rotated approximately 90 degrees from the position shown in FIG. 15.
Figure 15:
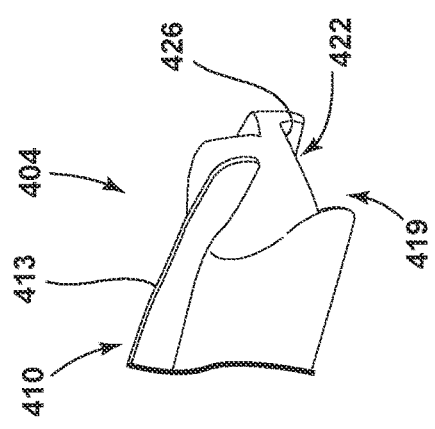
FIG. 15 is an enlarged and fragmentary perspective view of a further embodiment of the cutting head of the surgical accessory.

FIGS. 15 and 16 illustrate a further embodiment of the surgical accessory. Components of this embodiment which are similar or identical to components of the first-discussed embodiment will include the same reference numbers plus "300". This embodiment includes a cutting head 404 having two different tissue-treating areas 410 and 419 located along the periphery thereof. The first tissue-treating area 410 includes an abrading region with a single cutting surface 415 and corresponding flute 417, which cutting surface 415 and flute 417 are helically-oriented, but may alternatively extend linearly substantially parallel with the axis of the cutting head 404. The second tissue-treating area 419 includes a window 422. The window 422 in this embodiment includes a pair of opposed and facing cutting edges 423 and 424 which are substantially smooth and extend substantially linearly and also are substantially parallel with one another, and a distal cutting edge 426 oriented transversely between distal ends of the cutting edges 423 and 424. The distal cutting edge 426 in this embodiment is substantially linear. Further, the window 422 here is non-toothed, but may be provided with a tooth or a plurality of teeth on one or both of the cutting edges 423 and 424, and one example of a tooth provided on the edge 424 is shown in dotted lines in FIG. 16.

Figure 18:
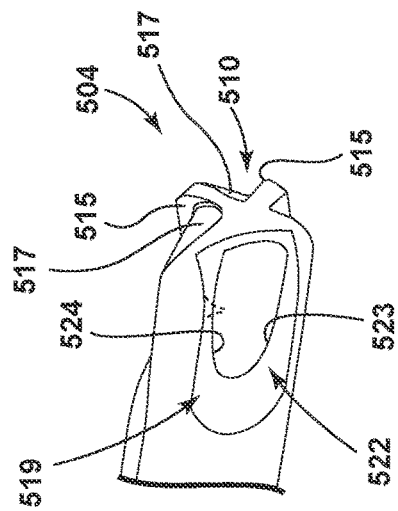
FIG. 18 is an enlarged and fragmentary perspective view of the cutting head of the surgical accessory rotated approximately 90 degrees from the position shown in FIG. 17.
Figure 17:
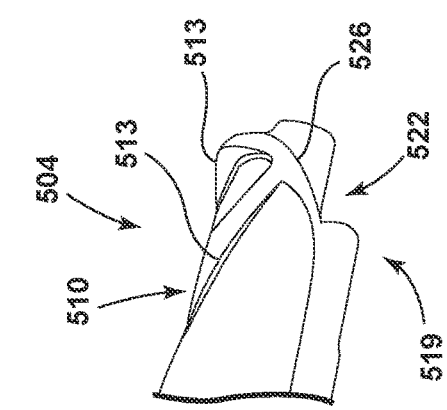
FIG. 17 is an enlarged and fragmentary perspective view of a further embodiment of the cutting head of the surgical accessory.

FIGS. 17 and 18 illustrate a yet another embodiment, and components thereof which are similar or identical to components of the first-discussed embodiment will include the same reference numbers plus "400". The cutting head 504 according to this embodiment comprises a first tissue-treating area 510 with an abrading region including two cutting surfaces 515 and corresponding flutes 517 provided opposite the window 522 of the second tissue-treating area 519. Here, the surfaces 515 and flutes 517 are helically-oriented, but may alternatively extend linearly substantially parallel with the axis of the cutting head 504. Further, the window 522 here is non-toothed, but may be provided with a tooth or a plurality of teeth on one or both of the edges 523 and 524, and one such tooth provided on the edge 524 is shown in dotted lines in FIG. 18.

Figure 20:
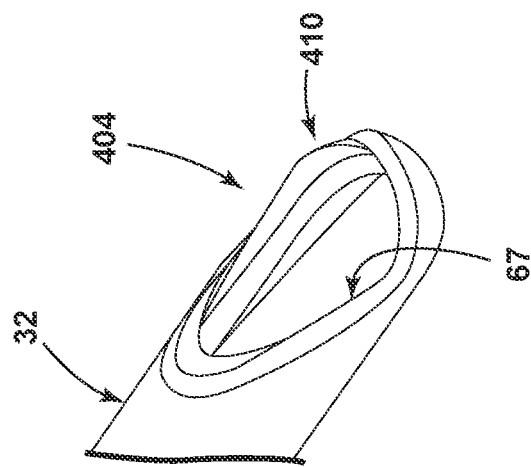
FIG. 20 is an enlarged and fragmentary perspective view similar to FIG. 19, but with the cutting element rotated approximately 180 degrees relative to the outer housing element from the position shown in FIG. 19.
Figure 19:
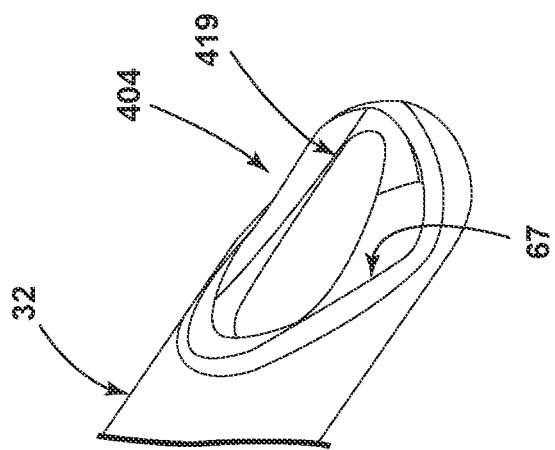
FIG. 19 is an enlarged and fragmentary perspective view of the embodiment of the cutting head of the surgical accessory shown in FIGS. 15 and 16, with the cutting element of the accessory located within the outer housing element.
Figure 53:
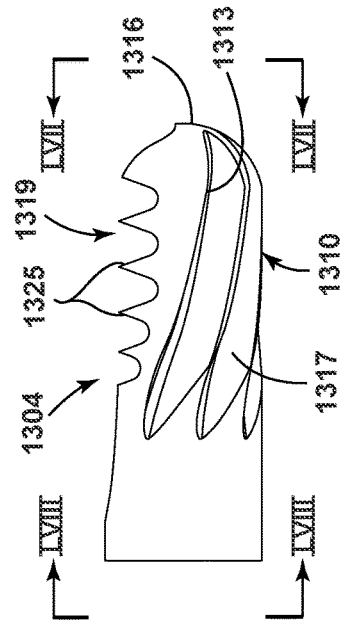
FIG. 53 is an enlarged perspective view of a further embodiment of the cutting head of the surgical accessory.
Figure 54:
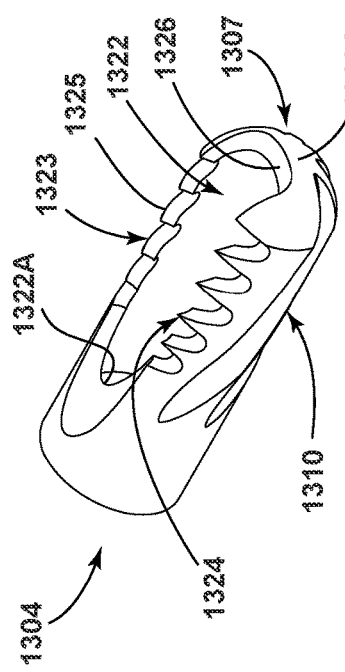
FIG. 54 is an enlarged plan view of the cutting head of the surgical accessory of FIG. 53.
Figure 55:
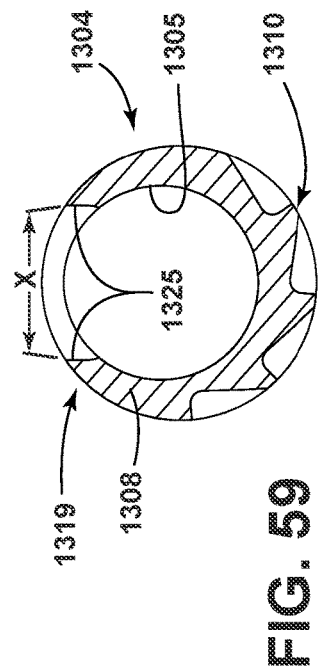
FIG. 55 is an enlarged view of the cutting head of the surgical accessory rotated approximately 180 degrees from the position shown in FIG. 54.
Figure 56:
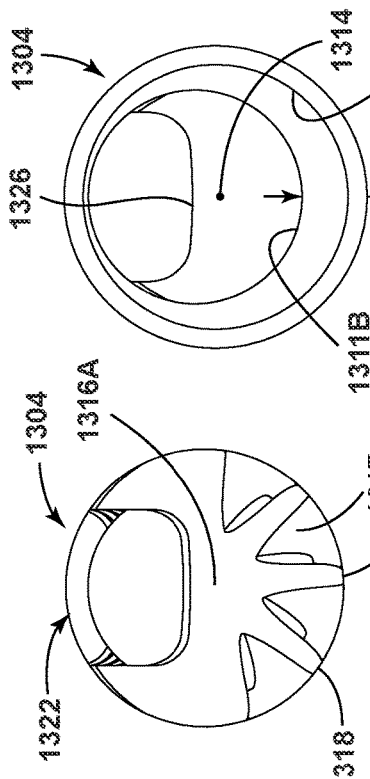
FIG. 56 is an enlarged view of the cutting head of the surgical accessory rotated approximately 90 degrees from the position shown in FIG. 54.

FIGS. 19 and 20 illustrate the cutting head 404 located interiorly of the outer housing element 32. It will be appreciated that the embodiment depicted in FIGS. 15-18 may be provided with lands similar to the lands 118 as illustrated in FIG. 10, or alternatively may be provided with relief angles and flats similar to angles C and flats 218 of the embodiment illustrated in FIG. 11. It will also be appreciated that any of the embodiments described herein which include a helically oriented cutting surface (or surfaces) and flute (or flutes) may alternatively include cutting features which extend not helically, but linearly or in a substantially straight manner longitudinally along the cutting head substantially parallel to, or at an angle relative to, the axis thereof.

FIGS. 21-24 illustrate a further embodiment of the surgical accessory, and components of this embodiment which are similar or identical to components of the first-described embodiment will include the same reference numbers plus "500", and a detailed description of all components will not be provided. As in the earlier described embodiments, the cutting head 604 of this embodiment incorporates two different types of tissue-treating areas 610 and 619 disposed in spaced-relation with one another along the periphery of the cutting head 604. The first tissue-treating area 610 of the cutting head 604 incorporates an abrading region which in this embodiment is generally similar to a rasp, and includes a plurality of teeth 640. Each of these teeth 640 at an outermost radial extent thereof defines an outer terminal edge 613, and each tooth 640 additionally includes a pair of cutting surfaces or faces 615 on opposite sides of the corresponding terminal edge 613 and facing away from one another. The arrangement of the teeth 640 as shown allows a similar type of cutting action in both the forward and reverse directions of rotation of the cutting head 604, which may be advantageous in that bone chips, for example during shoulder surgery, can be directed away from the endoscopic camera 10C in both right and left shoulder surgeries without sacrificing cutting speed. The second tissue-treating area 619 of this embodiment is substantially identical to the second tissue-treating area 119 of the first-described embodiment and will not be described further here. It will be appreciated that the tissue-treating area 619 may be toothed or non-toothed as described above relative to the area 119. Further, this embodiment includes lands 618, which function similarly to the lands 118 shown in the FIG. 10 embodiment.

FIGS. 25-29 illustrate a further embodiment of the surgical accessory which will now be described. Components of this embodiment which are similar or identical to components of the first-described embodiment will include the same reference numbers plus "600", and a detailed description of all components will accordingly not be provided. As in the prior embodiments, the cutting head 704 of this embodiment is provided with two different types of tissue-treating areas 710 and 719. In this embodiment, the first tissue-treating area 710 includes an abrading region in the form of abrasive particles 760. The abrasive particles 760, in the illustrated embodiment, are diamond grit particles 760. The diamond grit particles 760 may be synthetic diamond, but may also be of natural diamond. In order to accommodate these particles 760, the wall 708 of the cutting head 704 defines therein an outwardly opening recess 750 as best shown in FIG. 29, which recess 750 extends arcuately about a portion of the cutting head 704 in a circumferential direction and also extends axially along the cutting head 704 along a substantial portion of the length thereof. The recess 750 is defined along a periphery thereof by substantially flat faces 751 formed along the wall 708. As shown in FIGS. 27 and 29, the recess 750 does not penetrate radially through the wall 708, and instead terminates, in a radial direction, at an outwardly facing surface 752 of the wall 708 which defines a bottom of the recess 750. The surface 752 adjoins each of the faces 751 at lower terminal portions thereof, and the surface 752 and faces 751 together provide the recess 750 with a shallow and outwardly opening configuration.

The particles 760 are disposed within the recess 750 and are attached to the wall 708 of the cutting head 704. In one embodiment, the wall 708 is constructed of stainless steel, and the diamond grit particles 760 are attached to the wall 708 by use of a nickel plating 753. The use of the nickel plating 753 results in the diamond grit particles 760 being bonded to the stainless steel wall 708 via co-deposition that mechanically locks the particles 760 to the wall 708. The nickel plating 753 is electrodeposited onto the wall 708, and the diamond grit particles 760 are coated between about 50 and about 70% of their nominal diameter.

The wall 708 is coated with the particles 760 by creating a steel blank, which is masked so that only the intended area of the wall 708 is coated. The particles 760 and an initial nickel or nickel matrix layer are simultaneously co-deposited onto the blank in a nickel electrodeposition bath. The bath includes a nickel electrolyte solution and containers of diamond-grit particles submerged therein. The steel blank is positioned so that the surfaces that require coating are immersed in the layer of diamond-grit particles. A small initial layer of nickel is deposited onto the non-masked exterior surface of the blank via electrodeposition. This layer of nickel builds up around the diamond grit particles that are touching the blank and mechanically tacks them to the wall 708 within the recess 750. After a relatively thin layer of nickel has been built up on the wall 708, the part is removed from the electrodeposition bath and placed into another nickel electrodeposition bath that does not contain any diamond particles. The electrodeposition process continues until the nickel layer has reached the desired depth to ensure the diamond-grit particles 760 are securely bonded to the blank. In this regard and as shown in FIG. 29, the depth of the recess 750, the depth of the nickel plating layer 753 and the grit size of the particles 760 are chosen so that the particles 760 do not protrude beyond the outer diameter of the cutting head 704 in order to prevent wear on the outer housing element (not shown here) inside which the cutting head 704 is located. For larger diameter cutting accessories, such as those with a 5.5 mm outer diameter, the particles 760 may have a grit size of less than or equal to D252. For smaller diameter cutting accessories, such as those with a 4.0 mm outer diameter, the particles 760 may have a grit size of less than or equal to D151. Other grit sizes which may be utilized are D64, D76, and D107. The number included in the aforementioned grit sizes represents the nominal size of the diamond grit in micrometers. The grit sizes discussed above are only examples, and other grit sizes may be utilized. It will be appreciated that the embodiment depicted in FIGS. 25-29 may include a land, for example in the form of a strip which extends along the first tissue-treating area 719, which land includes an outer radial surface having an outer diameter which closely matches the inner diameter of the distal end of the outer housing tube so as to provide support between the cutting element and the outer housing element.

The second tissue-treating area 719 of this embodiment is substantially identical to the second tissue-treating area 119 of the first-described embodiment and will not be described further here.

FIGS. 30-35 illustrate a further embodiment of the surgical accessory which will now be described. Components of this embodiment which are similar or identical to components of the first-described embodiment will include the same reference numbers plus "700", and a detailed description of all components will accordingly not be provided. As in the first-described embodiment, the cutting head 804 is provided with two different types of tissue-treating areas. The first area 810 includes an abrading region having a bur configuration incorporating a fluted region with a plurality of cutting surfaces 815 and flutes 817 oriented in an alternating manner with one another along the circumference of the cutting head 804. The first tissue-treating area 810 of this embodiment has the flutes 817 and cutting surfaces 815 extending straight or linearly and substantially parallel with one another and with the axis 814 along a majority of the longitudinal extent of the distal end portion 807 of the cutting head 804. Each of the cutting surfaces 815 terminates at a cutting edge 813 which defines the radially outermost extent of the respective cutting surface 815. The cutting edges 813 extend in the proximal to distal direction and terminate adjacent the tip 816 of the distal end portion 807, as shown in FIGS. 30, 33 and 34. In this embodiment, the edges 813 terminate proximally of the tip 816, which effectively creates a bearing surface 816A at the tip 816, as in the embodiment shown in FIG. 9. It will be appreciated that the cutting surfaces 815 and the flutes 817 may alternatively be helically oriented as shown in dotted lines in FIG. 33.

In this embodiment, and as shown in FIGS. 30 and 34, the portions of the wall 808 of the cutting head 804 located between neighboring pairs of cutting surfaces 815 are provided with lands 818 as in the embodiment shown in FIG. 10, and serve to minimize wear on the interior surface of the housing tube of the outer housing element 32 due to movement of the cutting element relative thereto.

The cutting head 804, in an area spaced circumferentially from the first tissue-treating area 810, is provided with a second tissue-treating area 819 including a window 822 formed as an elongated opening in the cutting head 804. In this embodiment, the window 822 opens both sidewardly (or transversely) relative to the axis 814 and also distally, and communicates with the interior 805 of the cutting head 804. Opposite longitudinal sides of the window 822 define first and second cutting edges 823 and 824 located in substantially opposed, substantially facing and sidewardly (or circumferentially-spaced) relation with one another. The cutting edges 823 and 824 in this variation are substantially linear and parallel with one another, and are non-toothed. It will be appreciated that the window 822 may also be toothed along one or both of the edges 823 or 824. An example of one such tooth 825 provided on the edge 823 is shown in dotted lines in FIG. 31.

As shown in FIGS. 31 and 34, the window 822 additionally includes a distal cutting edge 826, which in this embodiment is substantially straight or linear and extends between and interconnects the first and second cutting edges 823 and 824.

The window 822 may be provided with varying geometries suitable for the type of tissue-treatment the cutting head 804 is intended to achieve. In this regard, if the window 822 is provided with a tooth or teeth 825, same may be provided with an internal shear angle based on the intended cutting action, as described above. Also, as shown in FIG. 35, the wall 808 in this embodiment has a thickness dimension 808A which is greater in the area of the first tissue-treating area 810 as compared to the thickness of the wall 808 in the region of the second tissue-treating area 819 which provides the cutting head 804 with increased rigidity and structural integrity to permit the formation of the cutting surfaces 815 and flutes 817. As also shown in FIG. 35, the cutting head 804 includes first and second bores 811A and 811B, which bore 811B is radially offset from the central axis 814 to provide the increased wall thickness of the wall 808 adjacent the first tissue-treating area 810. Alternatively, the second bore 811B may be provided with a non-circular configuration as shown in FIG. 10, with its axis aligned or offset from the axis, with a D-configuration, or with the configuration shown in FIG. 11. Still further, as an alternative to providing two bores within the cutting head 804, a single bore of a constant diameter can be provided in the cutting head 804, which single bore is of a diameter small enough to allow both a cutting window and flutes to be formed on the cutting head 804.

The embodiment illustrated in FIGS. 30-35 is useful for various types of surgery, such as shoulder, knee or hip surgery, but may be particularly suited for shoulder surgery. More specifically, it is often desirable in shoulder surgery to provide equal cutting action in both (opposite) directions of rotation of the cutting head 808, and the straight and parallel first and second cutting edges 823 and 824, along with the straight and parallel cutting edges 813 on opposite sides of each respective flute 817, allow for such balanced cutting or resection action.

FIGS. 36-42 illustrate another embodiment of the cutting accessory. Components of this embodiment which are similar or identical to components of the first-discussed embodiment will include the same reference numbers plus "800", and a detailed description of all components will therefore not be provided. The cutting head 904 according to this embodiment is provided with multiple tissue-treating areas. In this regard, a pair of first tissue-treating areas 910 and a pair of second tissue-treating areas 919 are provided on the cutting head 904, and these areas 910 and 919 are arranged in an alternating manner with one another along the periphery or circumference of the cutting head 904. Each of the first areas 910 includes an abrading region which is fluted and has a plurality of cutting surfaces 915 (and respective cutting edges 913) and flutes 917 oriented in an alternating manner with one another along the circumference of the cutting head 804. The flutes 917 and cutting surfaces 915 may be straight and substantially parallel with one another as shown or may be helically-oriented as shown in dotted lines in FIG. 39, based on the desired type of resecting action. The cutting edges 913 extend in the proximal to distal direction and terminate adjacent the tip 916 of the distal end portion 907. In this embodiment, the edges 913 extend close (in the distal direction) to the tip 916, which maximizes the area of the tissue-treating areas 910 available for use during surgery. Further, in this variation, and as best shown in FIG. 40, the portions of the wall 908 of the cutting head 904 located between neighboring pairs of cutting surfaces 915 are provided with lands 918 which serve to minimize wear on the outer housing element caused by movement of the cutting head 904 relative thereto.

Each of the window-type second tissue-treating areas 919 includes a window 922 formed as an elongated opening in the cutting head 904. Each window 922 opens both sidewardly (or transversely) relative to the axis 914 and distally, and communicates with the interior 905 of the cutting head 904. Opposite longitudinal sides of each window 922 define first and second cutting edges 923 and 924 located in substantially opposed and facing relation with one another. Each of the windows 922 additionally includes a distal cutting edge 926, which in this embodiment is substantially straight or linear and extends between and interconnects the corresponding first and second cutting edges 923 and 924.

Each of the windows 922 may be provided with varying geometries suitable for the type of tissue-treatment the cutting head 904 is intended to achieve. In this regard, the cutting edges 923 and 924 in this variation are substantially linear and parallel with one another, and are non-toothed. However, it will be appreciated that the windows 922 may be toothed along one or both edges thereof, and by way of example a plurality of teeth 925 are shown along the edge 923 in dotted lines in FIG. 37. If the window (or windows) 922 is provided with a tooth or teeth 925, same may be provided with an internal shear angle based on the intended cutting action, as described previously.

With reference to FIGS. 38, 41 and 42, the cutting head 904 includes first and second bores 911A and 911B which are centered on the axis 914. The first bore 911A as illustrated is sized to permit attachment of the cutting head 904 to the drive shaft 88. The second bore 911B is of a lesser diameter than the first bore 911A and results in the formation of a sufficient wall thickness at each of the first tissue-treating areas 910 to provide sufficient structural rigidity at these areas. More specifically, the wall 908 of the cutting head 904 at the areas 910 has a thickness dimension 908A which is substantially constant in the regions circumferentially between the windows 922 and proximally of the respective windows 922.

The embodiment depicted in FIGS. 36-42 includes a bearing surface 916A at the distal end 916 of the cutting head 904 which helps to support the cutting head 904 during movement relative to the outer housing element. If additional support for the cutting head 904 is desirable or necessary, the extent to which the windows 922 extend in the distal direction can be reduced in order to provide a larger bearing surface 916B, as shown in dotted lines in FIGS. 36 and 37. Additionally, with reference to FIGS. 36 and 40, the portions of the wall 908 of the cutting head 904 located between neighboring pairs of cutting surfaces 915 are provided with lands 918 which serve to minimize wear on the interior surface of the housing tube of the outer housing element 32 due to movement of the cutting head 904 relative thereto.

FIGS. 43-47 illustrate a further embodiment of the cutting accessory which will now be described. This embodiment includes a housing tube distal end 966 which is a variation of the distal end 66 of the housing tube 64 described previously, which distal end 966 can be utilized with any of the previously described cutting heads 104, 204, 304, 404, 504, 604, 704, 804 and 904. Additionally, FIGS. 46 and 47 illustrate a further embodiment of a cutting head 1004 assembled with the embodiment of the housing tube distal end 966 shown in FIGS. 43-45, which cutting head 1004 is similar to the cutting head 104 illustrated in FIGS. 5-12. It will be appreciated that the cutting head 1004 shown in FIGS. 46 and 47 may alternatively be utilized with a housing tube including the windowed distal end 66 described previously. Components depicted in FIGS. 43-47 which are similar or identical to components of the first-described embodiment will include the same reference numbers plus "900", and a detailed description of all components will accordingly not be provided.

The distal end 966 of the housing tube according to this variation is cut or formed to define a window 967 having an annular edge 968, which window 967 opens both sidewardly (or transversely) relative to the axis 931 and also opens distally. In forming the window 967, the wall of the distal end 966 of the housing tube is cut away or removed along the sides, and also distally, to a greater degree as compared to the window 67 formed on the distal end 66, which provides the distal end 966 with a scoop-like or spoon-shaped configuration. More specifically, and with reference to FIGS. 44, 46 and 47, the edge 968 of the distal end 966 of the outer housing element is arcuately curved so as to open upwardly on opposite sides of the distal end 966, and the edge 968 is also formed such that the distal end 966 terminates at a slightly upwardly projecting nose 968C. The edge 968 includes a pair of cutting edges 968A and 968B oriented in substantially opposed relation with one another and which are spaced circumferentially (or sidewardly-spaced) from one another along the distal end 966 of the housing tube. The annular edge 968, with its cutting edges 968A and 968B and nose 968C, is formed as a result of a cutting operation performed on the distal end 966 of the housing tube. The edges 968A and 968B effectively define free and circumferentially extending terminal edges of the housing tube so as to form respective sides of the window 967.

The cutting head 1004 of this embodiment is shown located within the distal end 966 of the outer housing element in FIGS. 46 and 47. The cutting head 1004 includes first and second tissue-treating areas 1010 and 1019. In this embodiment, the tissue treating area 1010 of the cutting head 1004 includes an abrading region with cutting edges 1013, cutting surfaces 1015 and flutes 1017 which extend further distally along the cutting head 1004 as compared to the edges 113, surfaces 115 and flutes 117 of the embodiment shown in FIGS. 5-9. This configuration of the cutting head 1004, in combination with the reduced-area of coverage provided by the scoop-shaped distal end 966 of the outer housing element, allows a greater portion of the cutting head 1004 to be used to treat hard tissue. In this regard, this embodiment frees up greater regions of the tissue-treating area 1010 of the cutting head 1004 so that hard tissue can be resected even at the very end of the cutting head 1004. The cutting head 1004 of FIGS. 46 and 47 may have helically-oriented flutes 1017 or may alternatively include straight or linear flutes 1017.

FIGS. 48-51 illustrate a further embodiment of the surgical cutting accessory. This embodiment includes a distal end 1066 of the housing tube which is a further variation of the distal end 66 described previously, which distal end 1066 can be utilized with any of the previously described cutting heads 104, 204, 304, 404, 504, 604, 704, 804, 904 and 1004. For illustrative purposes, FIGS. 50 and 51 depict the cutting head 1004 shown in FIGS. 46 and 47 assembled with the variation of the housing tube distal end 1066 shown in FIGS. 48 and 49. Components shown in FIGS. 48-51 which are similar or identical to components of the first-discussed embodiment will include the same reference numbers plus "1000", and a detailed description of all components will accordingly not be provided.

The distal end 1066 of the housing tube according to this variation is cut or formed to define a window 1067 having an edge 1068, which window 1067 opens both sidewardly (or transversely) relative to the axis 1031, and also opens distally (axially) to a greater extent as compared to the window 967 shown in the embodiment depicted in FIG. 43. In forming the window 1067, the wall of the distal end 1066 of the housing tube is cut to form a distal edge 1070 having an edge surface 1071 oriented perpendicular to the axis 1031, and so as to form an arcuate edge 1068 including a pair of sidewardly-spaced and upwardly-opening recesses or valleys 1072 which respectively adjoin to opposite upper ends of the edge surface 1071 and at these junctures define respective tooth-like structures or projections 1073 which serve as catches for tissue.

The cutting head 1004 shown in FIGS. 46 and 47 is shown assembled within the distal end 1066 of the outer housing element in FIGS. 49 and 50, as mentioned above. With reference to FIG. 50, this cutting head 1004 projects a short distance axially beyond the distal edge 1070 of the distal end 1066 of the housing tube. The reduced-area of coverage provided by the truncated and recessed distal end 1066 of the outer housing element allows a greater portion of the cutting head 1004 (or any of the previously-described cutting heads 104, 204, 304, 404, 504, 604, 704, 804 and 904) to be used to treat tissue, and effectively frees up greater regions of the tissue-treating area 1010 of the cutting head 1004 so that hard tissue can be resected even at the very end of the cutting head 1004. Further, the tooth-like structures 1073 of the distal end 1066 of the outer housing element serve to prevent (or at least minimize) soft tissue from sliding off of the end of the accessory during rotation of the cutting head 1004, and thus serve as tissue-catches.

FIG. 52 illustrates a variation of the drive shaft 88 of the first-described embodiment, and components depicted in FIG. 52 which are similar or identical to components of the first-described embodiment will include the same reference numbers plus "1100", and a detailed description of all components will accordingly not be provided. The drive shaft 1188 shown in FIG. 52 is a non-tubular solid shaft, which may be rigid or flexible. In this variation, the proximal end of the drive shaft 1188 (not shown) is fixed to the hub of the cutting element as described previously, and the distal end 1191 of the drive shaft 1188 is fixed to an inner surface of the wall 1208 of the cutting head 1204. It will be understood that the cutting head 1204 shown in the fragmentary view of FIG. 52 is intended to represent any of the previously-described cutting heads 104, 204, 304, 404, 504, 604, 704, 804, 904 and 1004 as the drive shaft 1188 may be utilized with any of these cutting heads, and that the distal end 1166 of the outer housing element shown in this figure is intended to represent any of the previously-described distal ends 66, 966 and 1066. As shown by the directional arrows in FIG. 52, in this embodiment suction is drawn through the window 1167 defined by the edge 1168 of the distal end of the outer housing element and the window 1222 of the second tissue-treating area of the cutting head 1204 when these windows 1167 and 1222 are aligned with one another during rotation of the cutting head 1204 relative to the outer housing element, and then continues on in the proximal direction through the outer housing element to the handpiece 11.

Figure 57:
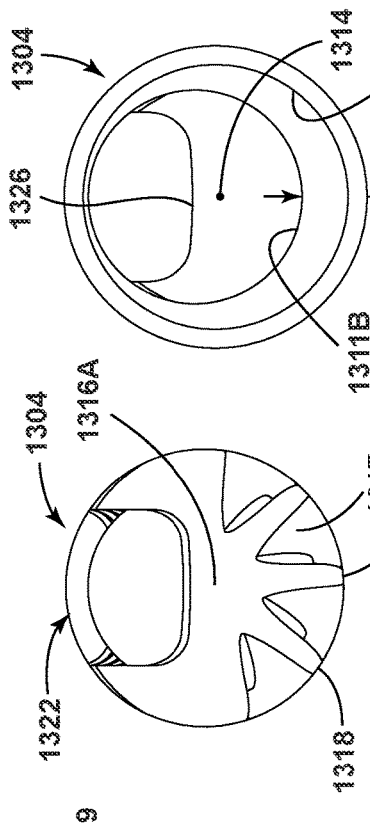
FIG. 57 is an enlarged distal end view as seen along line LVII-LVII in FIG. 56.

FIGS. 53-64 illustrate a further embodiment of the surgical accessory which will now be described. Components of this embodiment which are similar or identical to components of the first-described embodiment will include the same reference numbers plus "1200", and a detailed description of all components will not be provided. As in the prior embodiments, the cutting head 1304 includes different types of tissue treating areas 1310 and 1319. The first area 1310 has an abrading region with a bur configuration incorporating a fluted region with a plurality of cutting surfaces 1315 and flutes 1317 oriented in an alternating manner with one another along the circumference of the cutting head 1304. The first tissue-treating area 1310 in this embodiment has the flutes 1317 and cutting surfaces 1315 extending helically along a majority of the longitudinal extent of the distal end portion 1307 of the cutting head 1304. Further, the cutting edges 1313 of the respective cutting surfaces 1315 here extend in the proximal to distal direction and terminate proximally of the tip 1316 of the distal end portion 1307, as best shown in FIG. 57, to allow formation of the bearing surface 1316A. It will be appreciated that the cutting surfaces 1315 and the flutes 1317 may alternatively be straight or linear as shown in dotted lines in FIG. 55.

As shown in FIG. 57, the portions of the wall 1308 of the cutting head 1304 located between neighboring pairs of cutting surfaces 1315 are provided with lands 1318, which lands 118 serve to minimize wear on the interior surface of the outer housing element, as discussed previously.

The cutting head 1304, in an area spaced circumferentially from the first tissue-treating area 1310, is provided with a second tissue-treating area 1319 including a window 1322 formed as an elongated opening in the cutting head 1304. The window 1322 in this embodiment opens both sidewardly (transversely) and distally (axially), and communicates with the interior 1305 of the cutting head 1304. Opposite longitudinal sides of the window 1322 define first and second cutting edges 1323 and 1324 located in substantially opposed, substantially facing and sidewardly (or circumferentially-spaced) relation with one another. Each of the cutting edges 1323 and 1324 in this embodiment are toothed, and here a plurality of teeth 1325 are provided along each of the edges 1323 and 1324. Further, in this embodiment, each edge includes the same number of teeth 1325. It will be appreciated that a greater or lesser number of teeth 1325 than that shown may be provided along each edge 1323, 1324. Further, the edges 1323 and 1324 may not include the same number of teeth 1325. Additionally, only one of the edges 1323 or 1324 may be toothed, and the other edge may be non-toothed.

Figure 59:
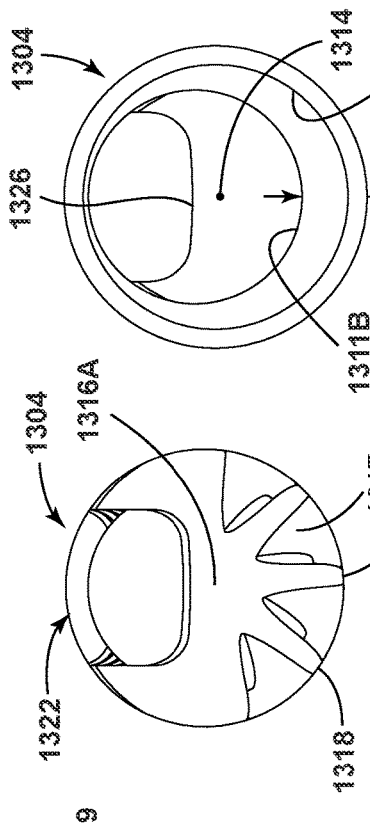
FIG. 59 is an enlarged cross-sectional view as seen generally along line LIX-LIX in FIG. 54.
Figure 63:
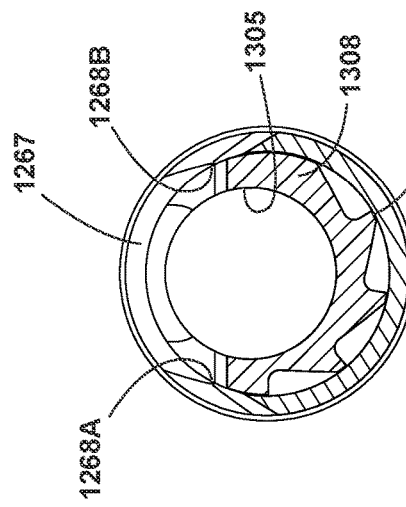
FIG. 63 is an enlarged cross-sectional view as seen generally along line LXIII-LXIII in FIG. 61.
Figure 64:
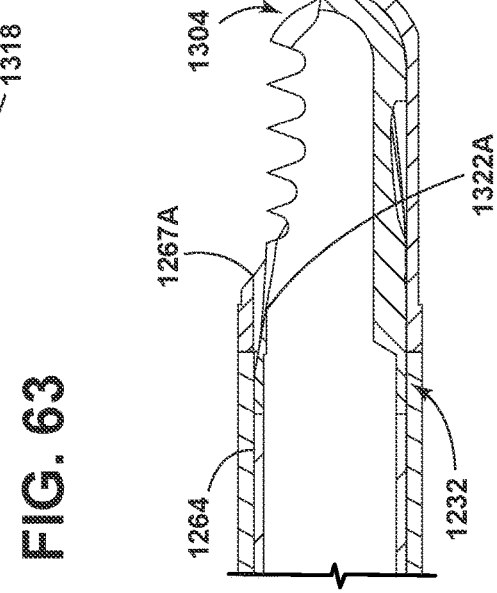
FIG. 64 is an enlarged cross-sectional view as seen generally along line LXIV-LXIV in FIG. 61.
Figure 60:
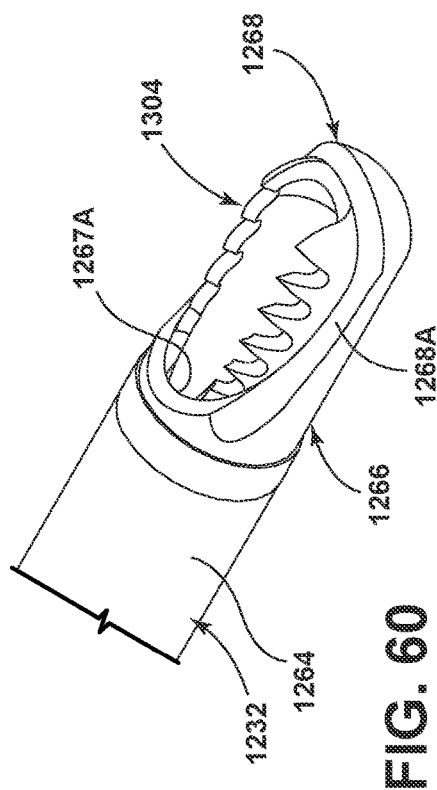
FIG. 60 is an enlarged and fragmentary perspective view of the cutting head of FIGS. 53-59, assembled within an outer housing element.
Figure 61:
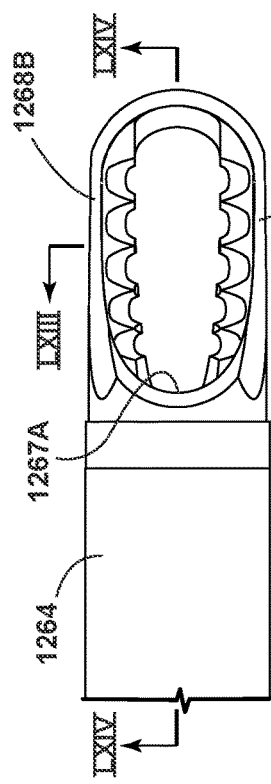
FIG. 61 is an enlarged and fragmentary plan view of the surgical accessory shown in FIG. 60.
Figure 62:
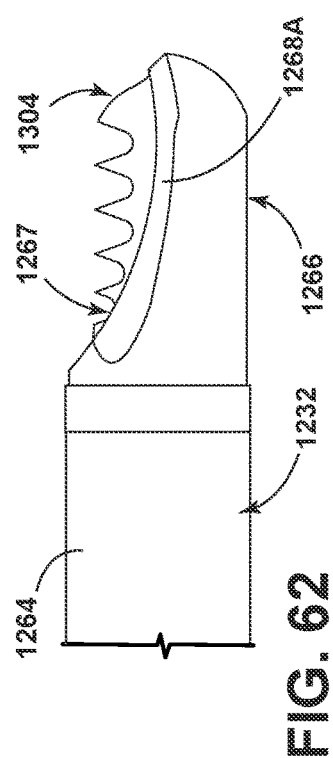
FIG. 62 is an enlarged and fragmentary view of the surgical accessory rotated approximately 90 degrees from the position shown in FIG. 61.

With reference to FIG. 59, the cutting window 1322 in this embodiment is provided with a geometry, and specifically a shear angle, which maximizes the tissue-treating ability of the cutting head 1304. Shear angle in this context is intended to refer to the opening angle of the window 1322 which is determined during the cutting process used to form the window 1322. In this regard, the edge of the cutting head 1304 which defines the window 1322 may be cut so as to provide the teeth 1325 with a negative internal shear angle which is less than zero degrees. This negative shear angle, when applied to cutting edges such as the teeth 1325, increases the likelihood that tissue will be scooped into the cutting window 1322, thereby increasing the consumption rate of the accessory. In the illustrated embodiment, the internal faces of the teeth 1325 are provided with an internal shear angle X, which angle X is less than zero degrees. In one embodiment, it may only be necessary to provide the tips of the teeth 1325 with this angle X, and not the entire internal face of the tooth 1325 (from root to tip). Further, it may be desirable to provide the teeth 1325 provided along the edge 1323 of the window 1322 of the cutting head 1304 with a larger size at their roots as compared to the teeth 1325 along the opposite edge 1324, so that these teeth are capable of withstanding the impact of hard tissue thereon (since the teeth 1325 along the edge 1323 are oriented in the hard-tissue resecting direction as determined by the rake direction of the first tissue-treating area 1310).

Figure 58:
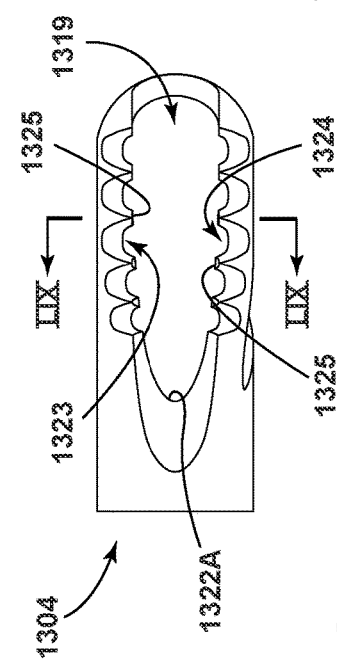
FIG. 58 is an enlarged proximal end view as seen along line LVIII-LVIII in FIG. 56.

As shown in FIGS. 58 and 59, the wall 1308 of the cutting head 1304 has a thickness dimension 1308A which is greater in the area of the first tissue-treating area 1310 as compared to the thickness of the wall 1308 in the region of the second tissue-treating area 1319, which provides the cutting head 1304 with increased rigidity and structural integrity to permit the formation of the cutting surfaces 1315 and flutes 1317. Additionally, the cutting head 1304 includes first and second bores 1311A and 1311B, which bore 1311B is radially offset from the central axis 1314 to provide the increased wall thickness of the wall 1308 adjacent the first tissue-treating area 1310. The second bore 1311B may alternatively be provided with a non-circular configuration as shown in FIG. 10, with its axis aligned or offset from the axis 1314, with a D-configuration, or with the configuration shown in FIG. 11. As an alternative to two bores provided within the cutting head 1304, a single bore of a diameter small enough to allow both a cutting window and flutes to be formed in the cutting head 1304.

FIGS. 60-64 illustrate the cutting head 1304 assembled within an outer housing element 1232. In this embodiment of the cutting head 1304, the window 1322 is of a longitudinal length which is greater than the longitudinal length of the window 1267 formed in the distal end 1266 of the outer housing element 1232. In this regard, when the cutting head 1304 is located within the outer housing element 1232, the most proximally-located part 1322A of the window 1322 of the cutting head 1304 is spaced proximally of the most proximal edge 1267A of the outer housing element window 1267. In some situations, tissue can snag or get caught in areas adjacent the proximal part 1322A of the window 1322, and this configuration may serve to minimize snagging or catching of tissue, which can potentially cause clogging of the accessory. It will be appreciated that the preceding embodiments of the surgical accessory described herein may incorporate the arrangement of the windows 1267 and 1322 of the outer housing element 1232 and the cutting head 1304 depicted in FIGS. 60-64. That is, the most proximally-located edge of the windows of the respective cutting heads described previously may be spaced proximally of the most proximally-located edge of the windows of the respective outer housing elements described previously.

Examples of Uses of the Systems and Methods in Combination with Medical Imaging of Tissue in the Surgical Site In various embodiments, the systems and methods described herein may be used in combination with medical imaging of tissue in the surgical site to facilitate the resection, removal or cutting of tissue and other surgical steps that may need to be performed. In various embodiments, methods employing medical imaging of the tissue (e.g., connective soft tissue or body structure, or connective hard tissue or body structure) alone or in combination with the systems and methods for resection, removal or cutting of tissue described in the various embodiments may be used in assessment of the tissue, diagnosis of the tissue or a combination thereof during pre-surgical intervention/examination, during surgical intervention/examination, or during post-surgical intervention/examination. Examples of various optical modalities in such applications include white light imaging, fluorescence imaging (e.g., using endogenous and exogenous fluorophores), or a combination thereof. The medical imaging may be performed in the visible region, near infrared region, or a combination thereof. In an embodiment comprising fluorescence medical imaging applications, an imaging agent for use in combination with the methods, systems, uses and kits described herein is a fluorescence imaging agent such as, for example, indocyanine green (ICG) dye. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

In some embodiments, the fluorescence imaging agent may be administered in various concentrations to achieve a desired circulating concentration in the blood or in other body tissue or fluid into which the fluorescence agent is administered or which it perfuses. For example, in embodiments where the fluorescence imaging agent is ICG, it may be administered at a concentration of about 2.5 mg/mL to achieve a circulating concentration of about 5 μM to about 10 μM in blood. In various embodiments, the upper concentration limit for the administration of the fluorescence imaging agent is the concentration at which the fluorescence imaging agent becomes clinically toxic in circulating blood or other body tissue or fluid, and the lower concentration limit is the instrumental limit for acquiring the signal intensity data arising from the fluorescence imaging agent circulating with blood or in other body tissue or fluid to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the methods described herein may comprise the step of administration of the imaging agent (e.g., a fluorescence imaging agent) to the subject and acquisition of the signal intensity data (e.g., video) prior to processing the signal intensity data where desired. In another aspect, the method may exclude any step of administering the imaging agent to the subject.

In an embodiment, a suitable fluorescence imaging agent for use in fluorescence imaging applications alone or in combination with other imaging to generate fluorescence image data of the tissue or body structure in the surgical site to be or being treated using the systems and methods described herein is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In some variations, the fluorescence imaging agent comprises a fluorescence dye, an analogue thereof, a derivative thereof, or a combination of these. A fluorescence dye includes any non-toxic fluorescence dye. In certain embodiments, the fluorescence dye emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength. In yet other embodiments, a fluorescence dye is any dye and derivatives thereof which facilitates imaging tissues including bone tissue, cartilage tissue, muscle tissue (e.g., tendons) or a combination thereof.

In an embodiment, the fluorescence imaging agent may be provided as a lyophilized powder, solid, or liquid (e.g., in a kit with the systems described herein or further with an imaging system used in combination with the systems described herein). In certain embodiments, the fluorescence imaging agent may be provided in a vial (e.g., a sterile vial), which may permit reconstitution to a suitable concentration by administering a sterile fluid with a sterile syringe for use as a kit with the systems and methods described herein as noted above. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality and the type of tissue (s) to be imaged.

In some variations, the fluorescence imaging agent used in combination with the methods, systems, uses and kits described herein may be used for blood flow imaging, tissue perfusion imaging, or a combination thereof, or to image tissue or a body structure (e.g., anatomy) (e.g., tissues of the joints and surrounding tissues in the surgical site) which may performed during an invasive surgical procedure, a minimally invasive surgical procedure, or a non-invasive surgical procedure in combination with invasive and minimally invasive procedures.

In various embodiments, the methods, systems, uses, fluorescence agents and kits may be used for tissue perfusion imaging. Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels.

An embodiment includes a kit for imaging tissue in a surgical site, with the kit comprising a fluorescence imaging agent and the system and methods described herein.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

The invention claimed is:

1. A surgical accessory comprising:
a cutting element shaft aligned along an axis, the cutting element shaft having a hollow interior passage therein; and
a cutting head extending from a distal end of the cutting element shaft along the axis, the cutting head having first, second, third and fourth tissue-treating areas separate from one another and circumferentially disposed on the cutting head,
wherein the first and second tissue-treating areas are configured to cut tissue having a first hardness and include respective first and second windows both in fluid communication with the hollow interior passage, at least part of each window defined by an edge on a circumferential outer surface of the cutting head, the edge being at a first radius from the axis of the cutting head, and
wherein the third and fourth tissue-treating areas are circumferentially separated by the first and second tissue-treating areas, the third and fourth tissue-treating areas being configured to cut tissue having a second hardness greater than the first hardness, each of the third and fourth tissue-treating areas having a fluted region including a plurality of flutes recessed relative to cutting edges on the circumferential outer surface of the cutting head, the cutting edges being at the first radius from the axis of the cutting head.

2. The surgical accessory of claim 1, wherein the hollow interior passage of the cutting element shaft extends into the cutting head such that at a first axial location on the cutting head, the cutting head has a first thickness from an edge of the first window to an edge of the second window.

3. The surgical accessory of claim 1, wherein the plurality of flutes are linearly oriented or helically oriented.

4. The surgical accessory of claim 1, wherein the cutting head has a first diameter in a first plane orthogonal to the axis, each of the first, second, third and fourth tissue-treating areas crossing the first plane, and a second diameter in a second plane orthogonal to the axis and adjacent to a distal tip of the cutting head, the second diameter being smaller than the first diameter.

5. The surgical accessory of claim 4, wherein the fluted regions of the third and fourth tissue-treating areas cross the second plane.

6. The surgical accessory of claim 1, wherein at least one fluted region has an outer periphery that is spaced apart from one of the first and second windows such that a smooth surface region separates the at least one fluted region and the first or second window.

7. A surgical accessory comprising:
a cutting element shaft aligned along an axis, the cutting element shaft having a hollow interior passage therein; and
a cutting head having a length extending from a distal end of the cutting element shaft along the axis to a distal tip, the cutting head having first, second, third and fourth tissue-treating areas circumferentially disposed on the cutting head and arranged so that each tissue-treating area is bounded by two of the other three tissue-treating areas,
wherein the first and second tissue-treating areas are configured to cut tissue having a first hardness and include respective first and second windows both in fluid communication with the hollow interior passage, at least one of the first window and the second window opening both radially relative to the axis and distally at the distal tip, and
wherein the third and fourth tissue-treating areas are separated by the first and second tissue-treating areas, the third and fourth tissue-treating areas being configured to cut tissue having a second hardness greater than the first hardness, each of the third and fourth tissue-treating areas having a fluted region.

8. The surgical accessory of claim 7, wherein the first window and the second window are linearly oriented parallel to the axis.

9. The surgical accessory of claim 7, wherein the cutting head includes a bearing surface at the distal tip of the cutting head, the bearing surface separating the first window from the second window.

10. The surgical accessory of claim 7, wherein the first window includes an outer edge abutting an outer surface of the cutting head and an inner edge abutting a hollow interior passage of the cutting head, the outer edge being longer than the inner edge.

11. The surgical accessory of claim 10, wherein the outer edge of the first window has a first proximal end and the inner edge of the first window has a second proximal end, the first proximal end being further from the distal tip than the second proximal end.

12. The surgical accessory of claim 7, wherein the first window is absent teeth.

13. The surgical accessory of claim 7, wherein each of the first, second, third and fourth tissue-treating areas cross a first plane orthogonal to the axis.

14. A surgical accessory comprising:
a cutting element shaft aligned along an axis, the cutting element shaft having a hollow interior passage therein; and
a cutting head extending from a distal end of the cutting element shaft along the axis, the cutting head having first, second, third and fourth tissue-treating areas separate from one another and circumferentially disposed on the cutting head such that each of the first, second, third and fourth tissue-treating areas cross a first plane orthogonal to the axis,
wherein the first and second tissue-treating areas are configured to cut tissue having a first hardness and are opposite one another, the first and second tissue-treating areas including respective first and second windows both in fluid communication with the hollow interior passage, the first and second windows being linearly oriented, and
wherein the third and fourth tissue-treating areas are configured to cut tissue having a second hardness greater than the first hardness, the third and fourth tissue-treating areas being opposite one another such that they are separated by the first and second tissue-treating areas, and the third and fourth tissue-treating areas each having an abrading region.

15. The surgical accessory of claim 14, wherein the third and fourth tissue-treating areas each have a fluted region.

16. The surgical accessory of claim 15, wherein at least one fluted region has an outer periphery that is spaced apart from one of the first and second windows such that a smooth surface region separates the at least one fluted region and the first or second window.

17. The surgical accessory of claim 14, wherein the cutting head includes a bearing surface at a distal tip of the cutting head, the bearing surface separating the first window from the second window.

18. The surgical accessory of claim 14, wherein the hollow interior passage of the cutting element shaft extends into the cutting head, the cutting head having a first inner diameter in a proximal portion of the cutting head and a second inner diameter in a distal portion of the cutting head, the second inner diameter being less than the first inner diameter.

19. The surgical accessory of claim 14, wherein the first and second windows have a first maximum length measured parallel to the axis and each of the abrading regions has a second maximum length measured parallel to the axis, the first length being greater than the second length.

20. The surgical accessory of claim 14, wherein the cutting head has a first diameter through the first plane and a tapering diameter through a distal end portion of the cutting head, the abrading region of the third and fourth tissue-treating areas having a length extending through both the first plane and at least part of the distal end portion.

* * * * *